United States Patent
Schrader et al.

(10) Patent No.: US 11,963,728 B2
(45) Date of Patent: Apr. 23, 2024

(54) MEDICAL HANDLING DEVICE AND METHOD FOR CONTROLLING A HANDLING DEVICE

(71) Applicant: KARL STORZ SE & Co. KG, Tuttlingen (DE)

(72) Inventors: Stephan Schrader, Tuttlingen (DE); Benedikt Koehler, Tuttlingen (DE); Chang-Hae Kim, Tuttlingen (DE); Marco Schulze, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 418 days.

(21) Appl. No.: 16/903,744

(22) Filed: Jun. 17, 2020

(65) Prior Publication Data
US 2020/0397234 A1 Dec. 24, 2020

(30) Foreign Application Priority Data

Jun. 19, 2019 (EP) .................................. 19181353

(51) Int. Cl.
*A61B 34/30* (2016.01)
*A61B 1/00* (2006.01)
(Continued)

(52) U.S. Cl.
CPC .......... *A61B 34/30* (2016.02); *A61B 1/00006* (2013.01); *A61B 1/00042* (2022.02);
(Continued)

(58) Field of Classification Search
CPC . A61B 34/35; A61B 1/00149; A61B 1/00006; A61B 34/74; A61B 50/20;
(Continued)

(56) References Cited

U.S. PATENT DOCUMENTS 5,696,837 A 12/1997 Green
6,331,181 B1 * 12/2001 Tierney .................. G16H 40/63
606/130

(Continued)

FOREIGN PATENT DOCUMENTS

AT 10676 U1 8/2009
CN 105517481 A 4/2016
(Continued)

OTHER PUBLICATIONS

Extended European Search Report for European Application No. 19181353.4, dated Jan. 7, 2020.
First Office Action (Including a machine Translation) for corresponding Chinese Patent Application No. 202010570774.3, mailed Nov. 29, 2023.

*Primary Examiner* — Stephen Holwerda
(74) *Attorney, Agent, or Firm* — Jason H. Vick; Sheridan Ross, PC

(57) ABSTRACT

A medical handling device which includes an instrument holder that supports and instrument and a robotic handling unit that supports the instrument hold, and a control device. The control device has a handling control unit that controls the robotic handling unit and an instrument control unit that controls the instrument. The control device has an interface for at least one input device. An input device is coupled to the interface. The input device is operable in a first operating mode to control the instrument and in a second operating mode to control the robotic handling unit. An enabling switch activates the second operating mode, in which the robotic handling unit is movable in response to input commands at the input device.

18 Claims, 12 Drawing Sheets

(51) Int. Cl.
*A61B 1/04* (2006.01)
*A61B 34/00* (2016.01)
*A61B 34/35* (2016.01)
*A61B 50/13* (2016.01)
*B25J 13/00* (2006.01)
*B25J 13/02* (2006.01)
*A61B 34/37* (2016.01)
*A61N 5/06* (2006.01)

(52) U.S. Cl.
CPC .......... *A61B 1/00149* (2013.01); *A61B 1/043* (2013.01); *A61B 34/35* (2016.02); *A61B 34/74* (2016.02); *A61B 50/13* (2016.02); *B25J 13/02* (2013.01); *A61B 1/00009* (2013.01); *A61B 1/00045* (2013.01); *A61B 1/00188* (2013.01); *A61B 1/00193* (2013.01); *A61B 34/37* (2016.02); *A61N 5/062* (2013.01)

(58) Field of Classification Search
CPC ... A61B 1/00039; A61B 90/361; A61B 50/13; A61B 34/30; A61B 1/00042; A61B 1/043; A61B 1/00045; A61B 34/37; A61B 1/00009; A61B 2034/742; A61B 1/00193; A61B 2090/371; A61B 34/32; A61B 1/00188; A61B 2017/00973; B25J 19/06; B25J 13/02; A61N 5/062
See application file for complete search history.

(56) References Cited

U.S. PATENT DOCUMENTS

| | | | |
|---|---|---|---|
| 9,079,317 | B2 | 7/2015 | Preisinger et al. |
| 10,806,533 | B2 | 10/2020 | Mustufa et al. |
| 11,653,985 | B2 | 5/2023 | Ishihara et al. |
| 2008/0234866 | A1* | 9/2008 | Kishi ..................... A61B 34/37 700/259 |
| 2009/0171374 | A1* | 7/2009 | Omori ..................... A61B 34/71 606/130 |
| 2009/0326322 | A1 | 12/2009 | Diolaiti |
| 2015/0085084 | A1 | 3/2015 | Heni et al. |
| 2016/0015476 | A1* | 1/2016 | Jagga ..................... G08C 17/02 606/1 |
| 2016/0135670 | A1 | 5/2016 | Bernhart et al. |
| 2017/0163972 | A1 | 6/2017 | Köhler et al. |
| 2018/0177523 | A1 | 6/2018 | Piron et al. |
| 2018/0263710 | A1 | 9/2018 | Sakaguchi et al. |

FOREIGN PATENT DOCUMENTS

| | | |
|---|---|---|
| CN | 108742483 A | 11/2018 |
| CN | 109009446 A | 12/2018 |
| CN | 109310480 A | 2/2019 |
| GB | 2568989 A | 6/2019 |
| GB | 2572256 A | 9/2019 |

* cited by examiner

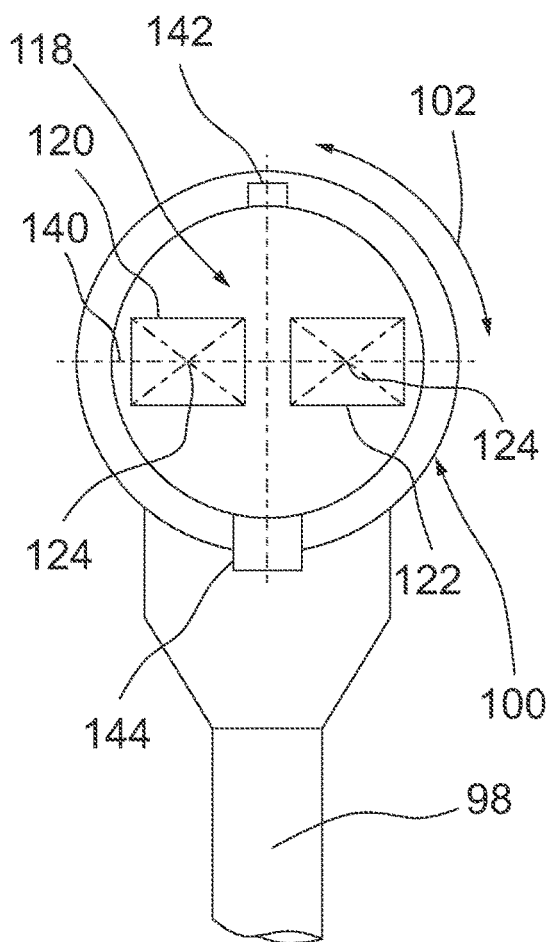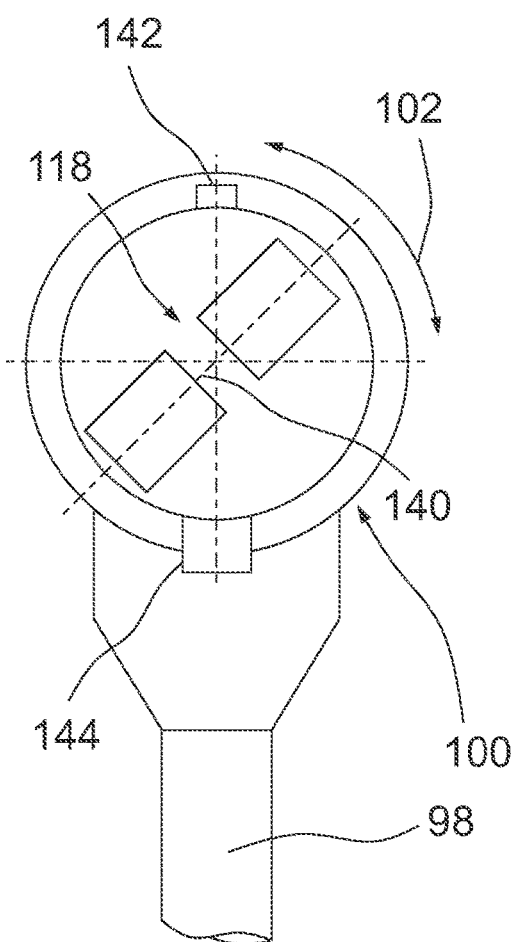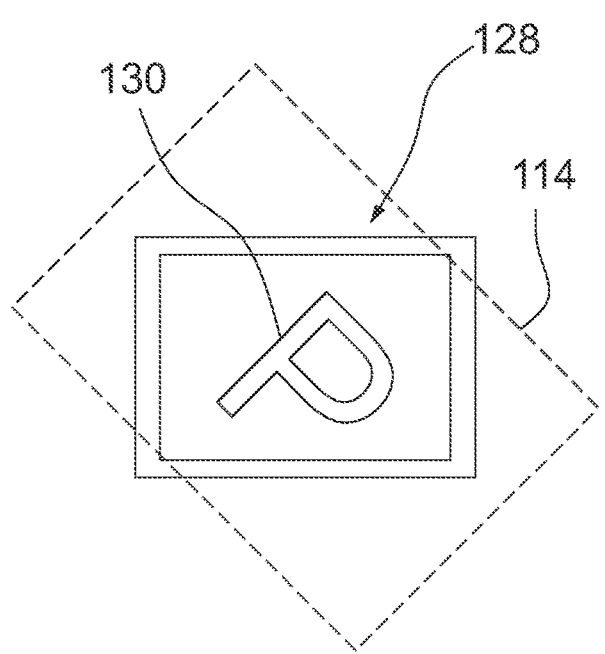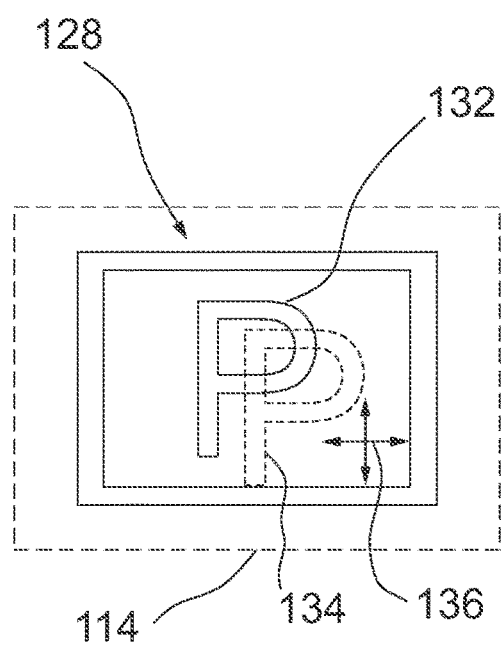
Fig. 3　　　　　　　　　　Fig. 4

MEDICAL HANDLING DEVICE AND METHOD FOR CONTROLLING A HANDLING DEVICE

CROSS-REFERENCE TO RELATED APPLICATIONS

This application claims priority from European patent application 19 181 353.4, filed on Jun. 19, 2019. The entire content of that priority application is incorporated herein by reference.

BACKGROUND

The present disclosure relates to a medical handling device and a method for controlling a handling device, wherein the handling device comprises a robotic handling unit, which carries an instrument holder for holding an instrument, for example an observation instrument, and wherein a handling control device is provided for controlling the robotic handling unit, which can be controlled via an input device.

US 2015/0085084 A1 discloses a medical instrument that is designed arranged as an observation instrument, which is arranged to capture an image of an object field on a human or animal body from outside the body, the instrument comprising a shaft and observation optics arranged at a distal end of the shaft for capturing the image of the object field, wherein the observation optic is arranged as a stereo optic with at least one electronic image capturing unit for capturing a stereo image of the object field, and wherein the instrument comprises an optical unit, which comprises the observation optic, and which is rotatable about a first axis of rotation approximately parallel to a viewing direction of the observation optic.

Such an observation instrument for observing an object field from outside the body is referred to as an exoscope. Furthermore, instruments, for instance observation instruments, are known, which are arranged as endoscopes for capturing an image inside the human or animal body.

US 2017/0163972 A1 discloses an observation device, which comprises an observation instrument and an input device that is arranged as a multi-axis input module for controlling the observation instrument. The input device is designed similar to a so-called space mouse. US 2017/0163972 A1 discloses the use of the input device for controlling imaging parameters as well as for controlling image reproduction parameters. An imaging parameter involves for example a focus adjustment. An image reproduction parameter involves for example a digital zoom.

For the purposes of present disclosure, a distal end of an element is an end that faces an observation object, such as a patient. In contrast, a proximal end of the element is an element that is facing away from the distal end and thus also from the observation object. In the case of a hand-guided instrument, the proximal end regularly faces the operator of the instrument. In the case of an instrument that is guided by means of a handling unit, the instrument is occasionally—but not necessarily—accommodated in the region of its proximal end at the handling unit, for example at a housing.

Furthermore, so-called tele-operational systems or tele-manipulation systems are known, in which an instrument in the form of an observation instrument or the like is held and remotely controlled by a manipulator, for example from U.S. Pat. No. 5,696,837 A.

Medical instruments, such as observation instruments in the form of an endoscope or an exoscope, are often hand-held and/or hand-guided. This may have the potential advantage that the user can intuitively and immediately adjust the direction of view, the object field and/or image section and other parameters of the image acquisition by positioning the instrument accordingly in space.

However, systems are also known, in which instruments are not hand-held or hand-guided, but are mounted on a tripod or boom. This has the advantage that no operator is required to hold the instrument manually in the desired position and orientation. It is conceivable that the instrument is arranged in a fixed position, for example, in order to permanently observe a certain same image section in a pre-selected object field during an operation.

Furthermore, it is also conceivable to arrange the instrument on a handling unit and/or manipulator (also referred to as a motorized holding system and/or robot) in order to use degrees of freedom of movement of the handling unit to move and align the instrument.

In this way, even if the instrument is not directly hand-held or hand-guided, the position, orientation and/or image section can be changed. However, this requires an operation to initiate the desired movement of the instrument.

Often, however, control elements are already provided for the instruments as such, e.g. control elements for controlling imaging parameters and/or image reproduction parameters of an image capturing system, which comprises an observation instrument having an image capturing unit, and a corresponding display for image reproduction. This means that even without additional movement of the instrument, various control operations are already conceivable, for which control elements are provided.

When automating and/or mechanically supporting medical activities, however, care must be taken to ensure that the systems as such are still intuitive, simple and safe to operate. For instance with telemedical systems and/or robotic systems, it must be considered that frequently no direct feedback to the operator is possible. This can lead to operating errors, in comparison to purely manual, hand-guided operation, if the operator is not immediately aware of the activity triggered by the operating command currently issued.

In view of this, it is an object of the present disclosure to present a medical handling device and a method for controlling a handling device, which enable intuitive and low-error control of a number of functions, at least in certain embodiments.

It is a further object of the present disclosure to present a medical handling device and a method for controlling a handling device that enable the use of a manageable number of input devices and/or input options to control a plurality of different functions, at least in certain embodiments.

It is a further object of the present disclosure to present a medical handling device and a method for controlling a handling device that prevent adverse interactions/interferences during operation, for instance in terms of operator control, at least in certain embodiments.

It is a further object of the present disclosure to present a medical handling device and a method for controlling a handling device that enable clear and concise operation and thus reduce the likelihood of operating errors, at least in certain embodiments.

It is a further object of the present disclosure to present a medical handling device that reduces distraction from the actual activity during operation/control, at least in certain embodiments.

It is a further object of the present disclosure to present a handling device, which optimizes the working conditions for the user/surgeon and helps the user to keep the overview, at least in certain embodiments.

SUMMARY

In regard of the medical handling device, these and other objects are achieved by a medical handling device, comprising:

an instrument holder for holding an instrument, a robotic handling unit that supports the instrument holder, a control device comprising a handling control unit for controlling the robotic handling unit and an instrument control unit for controlling the instrument wherein the control device comprises an interface for at least one input device, an input device that is coupled to the interface, wherein the input device is operable in a first operating mode for controlling the instrument and in a second operating mode for controlling the robotic handling unit, and an enabling switch to activate the second operating mode, in which the robotic handling unit is movable in response to input commands at the input device.

In this way, the object of the disclosure is completely achieved.

According to the invention, the enabling switch and the design of the control device ensure that the operator only operates the handling device intentionally, and not unconsciously, in the second operating mode. This increases safety during operation of the handling device. In the first operating mode, the operator can basically control functions of the instrument held on the instrument holder. In the case of an observation instrument, for example, this can relate to imaging parameters and/or image reproduction parameters, which can be controlled independently of the robotic handling unit.

In the second operating mode, however, the robotic handling unit is used, for example to change the position and/or orientation of the instrument in space. In the case of exemplary uses for medical diagnosis and/or treatment in the immediate vicinity of a patient, this can also include relative movements of the instrument with respect to the patient. In contrast, the first operating mode involves no or hardly any relative movement between the instrument and the patient. Accordingly, primarily in the second operating mode, there is a certain risk potential due to movements of the instrument. The second operating mode is used, for example, to change a displayed image section when using an observation instrument by moving the instrument relative to the observed object.

Against this background, it is therefore intended that the operator can only consciously activate the second operating mode by pressing the enabling switch. This prevents the operator from unconsciously activating the robotic handling unit for controlling (moving) the instrument in the first operating mode. The safety level when operating the handling device is increased.

Nevertheless, the operator can control various functions of the robotic handling device with one and the same input device. This applies to functions of the robotic handling unit that are controlled by the handling control unit. However, this also applies to instrument functions, which are controlled by the instrument control unit.

In this way, a separation between functions where the handling unit is possibly or where it is definitely moved, and functions where the handling unit is not moved is possible. This increases safety. This applies for instance when the operator controls the handling unit mediately (for example, without a direct view of the instrument), and is guided by a displayed image and not necessarily by the actual movements of elements of the handling unit and the instrument.

The robotic handling unit can also be referred to as a telemedical handling unit. Even if it is basically conceivable to operate the handling unit fully or partially automatically, control by the operator/surgeon is provided for in exemplary embodiments.

In general, the input device can be used to manipulate the displayed image section via user inputs, when an observation instrument is used. This can include a movement (translation or pivot motion). However, a rotation as well as an enlargement/reduction (zoom and/or change of the image scale) is also conceivable. Furthermore, it is conceivable to control a focus drive for adjusting a focal plane (plane of focus) via the input device.

The input device can be used for controlling the instrument but also for controlling the robotic handling unit. This simplifies the operation for the operator considerably. It is not absolutely necessary to use two separate input devices.

The instrument control unit can be referred to as CCU/controller/console. The input device for the manipulation (movement) of the image section in exemplary embodiments is connected to the instrument control unit via an interface. In other words, control commands for the handling control unit are transferred (in terms of signals) from the input device via the instrument control unit to the handling unit. Furthermore, the status of the image setting (zoom, focus, ROI position and image orientation) of the unit to be moved (e.g. exoscope) can be passed on to the handling unit via the CCU. The handling unit can then react accordingly, for example by changing the direction of movement when the orientation setting is changed, or by changing the pivoting radius when the focus setting is changed.

The control device can be distributed and thus comprise an instrument control unit for controlling the instrument and a separate handling control unit for controlling the robotic handling unit, which communicate with each other. It is to be understood that the distributed design can also be realized virtually (by software). Nevertheless, at least in exemplary embodiments, a hardware separation of instrument control unit and handling control unit is conceivable. In this way, the instrument control unit (CCU/console) remains universally usable, i.e. also for hand-held/hand-guided instruments.

According to an exemplary embodiment of the handling device, the instrument is arranged as an observation instrument. For example, the observation instrument is an instrument for observing the body from outside the body. This is not to be understood as to be limiting. In alternative embodiments, the observation instrument is an instrument for observing the inside of the body, e.g. an endoscope or a laparoscope. Nevertheless, it is also conceivable to mount other instruments, which are not observation instruments, on the instrument holder of the robotic handling unit.

According to an exemplary embodiment of the handling device, the input device can be coupled to the control device, wherein the control device can be coupled to the instrument and to the robotic handling unit, and wherein the control device is interposed between the input device and the instrument mounted on the instrument holder. In other words, in exemplary embodiments the control device is interposed between the input device and the instrument in terms of signals. In this embodiment, the signal exchange between the input device and the instrument takes place using the control device.

Both the first operating mode and the second operating mode use the same lines and signal paths, at least in exemplary embodiments.

According to another exemplary embodiment of the handling device, the control device is interposed between the input device and the robotic handling unit, in terms of signals. Furthermore, in this embodiment, the instrument control unit is arranged—in terms of signals—between the observation instrument and the input device. Signals are transmitted via the instrument control unit and/or, if necessary, even looped through.

In an exemplary embodiment, it is also provided that the input device (in the case of controlling an imaging parameter directly at the observation instrument) can be connected—in terms of signals—to the observation instrument via the robotic handling unit.

An aspect of present disclosure is based on the fact that the handling control unit controls the robotic handling unit depending on parameters of the observation instrument. This can for instance relate to parameters of an observation head/camera head of the observation instrument. For example, the handling control unit can control the travel speed of the links of the robotic handling unit as a function of a given magnification level (zoom factor, focus distance and/or object distance). For example, with a large zoom factor and/or a small object distance (corresponding to a detailed representation) the travel speed of the robotic handling unit can be reduced. Accordingly, the traversing speed of the robotic handling unit can be increased, for example, with a small zoom factor and/or a large object distance (corresponding to an overview display).

An aspect of present disclosure relates to the use of parameters or characteristic values, which characterize the observation instrument and its operation, for the control of the robotic handling unit by the handling control unit. This means that the signals and information used overlap and may even influence each other.

Nevertheless, at least in exemplary embodiments it is intended that the observation instrument and the instrument control unit can be used separately from the handling device. This applies for instance to so-called hand-held/hand-guided applications. Thus, synergies between the handling unit and the observation instrument and/or between the handling control unit and the instrument control unit can be exploited. On the other hand, the observation instrument can still to be used autonomously without the necessity to provide the handling unit.

According to another exemplary embodiment of the handling device, the enabling switch comprises two states 0 and I, a first state 0 being an initial state and a second state I being an activation state for the second operating mode. Accordingly, the enabling switch comprises at least one input element with two (or more) switching stages. The first state 0 corresponds, for example, to a state, in which the enabling switch is not influenced/actuated by the operator.

By acting on the input element of the enabling switch, the enabling switch can be changed from the first state 0 to the second state I. In the second state, the second operating mode is activated, so that the operator can control the handling unit via the input device.

According to a further exemplary embodiment of the handling device, the enabling switch also comprises a third state II, wherein the enabling switch, for instance during the activation, can be transferred starting from the first state 0 by applying an actuating force first into the second state I and then, with increased actuating force, into the third state II, and wherein the controlling of the robotic handling unit is blocked both in the first state 0 and in the third state II of the enabling switch. In this way, the operational safety is further increased. This function can also be referred to as a panic function. For example, if the operator applies too much actuating force, the enabling switch is changed to the third state II, in which the second operating mode (for controlling the handling unit via the input device) is deactivated.

This takes into account, for example, situations, in which the operator unintentionally acts on the enabling switch. In the case of a footswitch, for example, this can happen if the operator steps on the input element of the footswitch without intention. In other words, the operator must hold the enabling switch in the second state I to be able to control the handling unit to move the instrument via the input device. Therefore, if a higher force is applied, the second mode is deactivated. This also occurs if the enabling switch is unconsciously operated with a high force.

In other words, for example, a force range with an upper limit and a lower limit is defined, in which the enabling switch is in the second state I to enable the second operating mode. If the operator acts on the enabling switch with a lower force, the enabling switch remains in the first state 0. The second operating mode is not enabled. Conversely, if the operator acts on the enabling switch with a higher force, the upper limit of the force range is exceeded. The enabling switch is transferred to the third state II. The second operating mode is not enabled and/or the second operating mode is deactivated. In this way, the risk of operating errors can be further reduced.

According to another exemplary embodiment of the handling device, the second state I of the enabling switch, in terms of switching positions of an input element of the enabling switch, is arranged between the first state 0 and the third state II.

According to another exemplary embodiment of the handling device, the enabling switch is directly connected to the handling control unit of the control device, which is assigned to the robotic handling unit. In this way, a proprietary safety device (enable control) is created, which cannot simply be bypassed/deactivated by software. This further increases security.

As an example, the enabling switch is hard-wired to the control device of the handling device, for instance to a safety device there. The enabling switch is—in terms of signals—directly coupled to the safety device/enable control. This reduces the risk of manipulation. In other words, it is conceivable to design the enabling switch and/or the safety device discretely (using discrete and, if necessary, proprietary elements).

According to another exemplary embodiment of the handling device, the control device is adapted to provide control commands, which have been detected in the second operating mode via the input device, for the robotic handling unit to the handling control unit via the instrument control unit. This takes account of the fact that the instrument, for example the observation instrument, can in principle also be used without the robotic handling unit, e.g. for hand-held/hand-guided applications. In such a case, the input device is primarily used for instrument control. In this respect, in exemplary embodiments, a coupling of the input device with the instrument control unit is provided. The use of this input device for controlling the handling unit, i.e. for generating operating signals, which are processed by the handling control unit, takes place in the second operating mode and is enabled by the enabling switch.

According to a further exemplary embodiment of the handling device, the control commands for the robotic handling unit in the second operating mode are transmitted via the instrument control unit, which forwards the control commands. This also takes into account the fact that the instrument can be used independently without the robotic handling unit, at least in exemplary embodiments. Nevertheless, the control device has a simple structure, with sufficient consideration given to operating safety and the avoidance of operating errors.

According to a further exemplary embodiment of the handling device, the input device is arranged as a multi-axis input device, wherein the input device records operating movements in the form of travel motions or pivot motions in at least two axes, and wherein the operating movements are converted into control commands for the robotic handling unit.

According to another embodiment of the handling device, the robotic handling unit comprises a multi-link kinematics with a plurality of coupling links, wherein the control device is adapted to convert the movement instructions into control commands for movement axes of the coupling links by means of interpolation. In this way, a multi-axis handling unit can also be controlled in a simple way by operating the input device. For example, the multi-link kinematics is a serial kinematics. It is to be noted that parallel or mixed serial-parallel kinematics can also be used.

According to another exemplary embodiment of the handling device, the robotic handling unit comprises a serial kinematics with a plurality of coupling links, which are controlled by the handling control unit of the control device. This allows the observation instrument to be moved in a controlled manner with great freedom of movement in a given space.

According to another exemplary embodiment of the handling device, the control device is adapted to store a current position and orientation of the instrument and to recall it upon request. This function can also be referred to as save-and-recall function. In this way, the operator can set at least one waypoint, which can again be reached, as needed, from a position of the instrument that has been approached in the meantime. It is conceivable to provide specific function keys on the input device for this purpose, in order to store the position and recall it later.

This function can also be referred to as the recall function. In addition, it is conceivable that when an observation instrument is used simultaneously, not only the spatial position of the instrument but also its image parameters (for example, zoom, focus value and ROI position) are stored and can be recalled and set again if necessary with the appropriate command ("Recall"). This also applies to parameters of instruments, which are not observation instruments.

In general, the recall function can affect other parameters, such as parameters related to focus position, zoom, image section (for a pan function), and other image settings such as contrast, brightness and filter. This means that other parameters of the instrument or observation instrument can also be stored with this function and recalled upon request.

This function can be linked to the release via the enabling switch. It is therefore conceivable to allow save and recall only if the enabling switch enables the second operating mode of the handling device.

In an exemplary embodiment, this function includes storing and approaching of certain positions and orientations upon request, without the path covered being defined. In another exemplary embodiment, this function includes a kind of "backward movement", in which the handling unit not only moves to the position/orientation, but also travels the intermediate movement path in the opposite direction. Something like that may be used in a so-called direct control mode, for example.

According to another exemplary embodiment of the handling device, the control device is adapted to store a number of predefined positions and orientations of the instrument in order to recall them upon request. In this way, the save-and-recall function can move to several positions/orientations upon request. The control can be performed via an input device. In principle, it is conceivable to use several input devices, for example a touch monitor and/or a keyboard. In this way, even selection decisions with several choices can be made easily and directly.

According to a further exemplary embodiment of the handling device, the control device is adapted to operate the robotic handling unit in a direct control mode in order to move and align the instrument in space, wherein operating commands can be generated at the robotic handling unit by acting on an element of the handling unit that is adjacent to the instrument, and wherein the handling control unit is adapted to control the robotic handling unit in such a way that the observation instrument follows the induced movement.

Such a direct control mode ("direct drag mode") can be used for instance for the rough positioning of the observation instrument in relation to the object and/or object field. If the robotic handling unit is controlled in a suitable way, a quasi-manual adjustment directly on the instrument holder or at least in the vicinity of the observation instrument is possible.

In such a mode, the instrument holder with the observation instrument mounted thereon can therefore be moved and aligned quasi-manually in space, wherein the control device is adapted to hold the robotic handling unit in the current position/orientation automatically, but to enable manual (quasi-manual) movement by direct gripping and moving.

It is conceivable to monitor the drives of the elements/links of the kinematic chain of the robotic handling unit in the direct control mode in such a way that the operating commands are detected. In this way, the aforementioned "tracking movement" can be generated. In other words, in the direct control mode, the robotic handling unit itself serves as an input device.

In this mode, it is not absolutely necessary from the point of view of the robotic handling unit to request extensive information relating to the observation instrument, since the movement is manually induced and controlled directly at the robotic handling unit.

The direct control mode may include direct force application by the operator to an element of the robotic handling unit, for instance adjacent to the instrument holder. In this way, the robotic handling unit itself serves as an input device.

According to a further exemplary embodiment of the handling device, an operating element for controlling the robotic handling unit in the direct control mode is provided, wherein the operating element comprises a sensor for generating an enabling signal for the direct control mode. In other words, for the direct control mode it is not necessarily necessary to enable the second operating mode via the enabling switch. For example, the sensor is arranged as a kind of proximity sensor or touch sensor.

Preferably one and the same input element (e.g. a mushroom-shaped button or a lever similar to a joystick) is used for detecting the induced movements in the direct control mode, but also (e.g. via an integrated sensor) for enabling the direct control mode.

It is to be noted that according to an alternative embodiment, the release of the direct control mode can also be achieved via a separate element, i.e. a separate enabling switch, wherein the enabling switch for the direct control mode does not necessarily have to correspond to the enabling switch for the second operating mode.

According to another exemplary embodiment, when switching between the direct control mode and the control mode using the separate input device, a new release via the enabling switch is required. This ensures that the change between direct control in the direct control mode and indirect control via the input device is unambiguous.

In an exemplary refinement of this embodiment, an input device with an input element is provided to control the handling unit and thus the observation instrument in the direct control mode. The input device is placed directly on an element of the handling unit and for instance adjacent to the instrument holder and/or the mounted instrument. The input device and/or its input element itself can basically have a simple design. It may be a handle, which the operator can use to move/manipulate the handling unit by pulling, pushing or similar means.

According to another exemplary embodiment of the handling device, the robotic handling unit is mounted on a cart, wherein controlling the robotic handling unit to move the instrument is only possible when the cart (and/or a movement of the cart) is blocked. This measure further increases safety. In this way, relative movements of the cart in relation to the patient are avoided, which would also lead to a relative movement of the instrument in relation to the patient.

The blockage can be achieved by means of a lock or a support. By way of example, a support that lifts the cart (or alternatively a chassis) until the cart is stationary is conceivable. The function of the lock/support can be monitored via a locking sensor. The support can also be generally referred to as a travel lock.

In a further exemplary embodiment of the handling device, a sensor (blockage sensor) is also provided, which monitors the travel lock of the cart in order to determine a corresponding signal to the control device and/or a safety device. In an exemplary embodiment, the blockage sensor is coupled to a safety device of the control device via a discrete circuit. In this example, the blockage sensor is therefore permanently connected to the safety device. A design with proprietary elements is suitable. In this way, the monitoring of the blockade of the car can be monitored in a tamper-proof manner.

It is conceivable to combine the enabling switch with the blockade sensor in a circuit in order to bundle the safety functions. Here, too, discrete switching, design and coupling of the elements is conceivable, at least in exemplary embodiments.

According to a further exemplary embodiment of the handling device, the interface can be coupled with a plurality of input devices, via which the robotic handling unit is controllable, wherein the input devices can be prioritized differently. In this way, desired redundancies can be created. For example, in case of an emergency, a master input device can override another input device and/or cancel its commands.

Furthermore, the handling device can be controlled by different persons working together. Thus, it is conceivable that the command authority for controlling the handling device during a medical procedure is exercised by different persons in phases. Furthermore, it is conceivable that different input devices are arranged at different places/positions in relation to the patient and/or his support. This allows controlling from different perspectives.

As already mentioned above, various operating modes are conceivable. This basically also includes operation with different types of input devices. For example, it is conceivable to control the handling device via a single-handed input device. It is also conceivable to control the handling device via a touch monitor and/or a keyboard in combination with a monitor. In addition, it is conceivable to control the handling device, for instance its robotic handling unit, at least in a direct control mode by means of a force application on the handling unit itself. It is to be noted that, depending on the type of controlling selected, not necessarily all functions of the handling device can be controlled.

According to a further exemplary embodiment of the handling device, the control device is adapted to detect a present orientation of the image capturing unit and, depending thereon, to perform a mapping between an input device coordinate system and a coordinate system of the handling unit, which reflects the orientation of the image capturing unit. Accordingly, the orientation describes the horizon and/or the rotational position of the image capturing unit.

In other words, it is conceivable, at least in some embodiments, that a right-left axis of the input device causes a right-left movement of the displayed image section. Similarly, a forward-back axis of the input device can cause a forward-back and/or up-down movement of the displayed image section. This also applies to corresponding pivot motions, for example. By way of example, the information relating to the current orientation of the image capturing unit is transmitted from the observation instrument to the control device.

The control of the robotic handling unit now takes place under the condition that the orientation of the image capturing unit (the artificial horizon of the displayed image section) is maintained. A corresponding interpolation of the movement over different axes of the handling unit contributes to the maintenance of this mapping.

According to another exemplary embodiment of the handling device, the observation instrument comprises an orientation sensor for detecting the orientation of the image capturing unit. In this way, the artificial horizon and/or the image capturing unit's own coordinate system can be detected, in terms of signals.

In a further exemplary embodiment, the detection of the present orientation of the image capturing unit is done indirectly via the display, in which the desired orientation (horizon position) is defined based on the displayed image section. It is also conceivable to detect the orientation of the image capturing unit indirectly via a controlling of a drive for rotation/turning of the image capturing unit. Accordingly, the orientation is not captured by a sensor, but is derived from the target specifications for the drive.

For instance with an image capturing unit with one observation channel (mono image sensor), a solely digital rotation and detection of the horizon is also conceivable.

According to a further exemplary embodiment of the handling device, the control device is adapted to control the robotic handling unit under consideration of the present orientation of the observation instrument in such a way that the observation instrument can be moved along a spherical shell surface or a spherical shell segment surface. The movement takes place along a spherical shell or a spherical shell segment surface with a radius that is at least substantially constant with respect to the pivot point.

According to a further exemplary embodiment of the handling device, the control device is adapted to adjust the orientation of the image capturing unit during the movement of the observation instrument, while taking into account the path of movement. In this way, the orientation of the optical axis towards the pivot point (at least towards an adjacent area) can be achieved. The observation instrument, for instance its image capturing unit, is/are oriented radially towards the center of the orbital movement.

According to another exemplary embodiment of the handling device, the control device is adapted to control the robotic handling unit under consideration of the present orientation of the observation instrument in such a way that the observation instrument can be moved along a plane parallel to the observation plane. This is for instance done while taking into account the alignment of the observation instrument, for instance an image capturing unit thereof.

According to another exemplary embodiment of the handling device, the control device is adapted to control the handling unit in such a way that the instrument can be pivoted around a virtual pivot axis by interpolated movement of the handling unit, which is arranged parallel to the image capturing unit. In this way, an instrument (observation instrument) with variable viewing direction can be "simulated". Instruments without an integrated pivot drive can thus also provide such a degree of freedom and/or function. It is to be noted that this function is for instance conceivable with instruments that are arranged outside the patient's body.

It is conceivable that in alternative embodiments instruments with variable viewing direction and corresponding (internal) drives are provided, wherein the controlling of the drives is also performed via the input device. In this way, an intuitive controlling of the rotary actuator can take place.

According to another exemplary embodiment of the handling device, the control device is adapted to detect a type of instrument and to control the robotic handling unit depending on the detected type. This includes, for example, controlling the handling unit by the handling control unit and detecting/determining the type of the instrument by the instrument control unit.

By way of example, the control device is adapted to recognize different types of instruments, for example by means of identification information (ID), wherein the control device uses a configuration adapted to the respective type of instrument to control the handling unit and the instrument. According to a further exemplary embodiment, the instrument holder is adapted to hold different instruments. By way of example, an interface is arranged on the instrument holder, to which the instrument is coupled, in terms of signals, so that configuration information and/or identification information can be queried via this interface.

According to another exemplary embodiment of the handling device, the image capturing unit can be rotated in the instrument arranged as an observation instrument. This relates for instance to an axis perpendicular to the image plane of the image capturing unit. Exemplary embodiments with stereo image capturing unit use such a function. It is basically conceivable to design the image capturing unit to be manually rotatable. However, it is also conceivable to provide a rotary drive/rotary drive for the image capturing unit. The rotatability of the image capturing unit allows for image erection.

According to another exemplary embodiment of the handling device, the observation instrument comprises a stereo image capturing unit, for instance with two image sensors.

In such a case, the image erection via the rotatability of the image capturing unit is potentially advantageous. In this way, the alignment of the observation channels with the human eye area can be achieved. Embodiments with more than two image sensors are also conceivable, e.g. if two sensors are assigned to a spectral range (visible light, infrared, etc.).

According to another exemplary embodiment of the handling device, the control device is adapted to map between the orientation of the image capturing unit and movement axes for input at the input device in such a way that directions of movement of the image section displayed by the display unit are brought into alignment with direction instructions at the input device. In this way, it is not necessary for the operator to make a notional alignment between the different coordinate systems/orientations. The operator can primarily use the displayed image section to move it in the desired way.

Accordingly, the implementation of the operating commands (direction commands and travel commands) by the control device includes a transformation of coordinates, which is taken into account in the control of the handling unit. The movement axes correspond, for example, to corresponding degrees of freedom of movement (forwards, backwards, right, left, etc.).

According to another exemplary embodiment of the handling device, the input device is arranged as a multi-axis input device, for instance as a single-handed multi-axis input device, wherein the input device allows operating movements in the form of travel motions or pivot motions in at least two axes to capture movement signals for movement of the image section along a spherical surface. The input device can be arranged as a so-called 3D mouse. By suitable action on the input device, for instance on an actuating element of the input device, the movement of the image section can be controlled, for example along a spherical surface or spherical section surface. From the point of view of the observer of a display unit, for example a monitor, the input device with the image capturing unit is moved two-dimensionally along a flat pattern of the curved surface. It is understood that the real movement takes place in three-dimensional space. Furthermore, in another mode, it is conceivable to control the movement of the image section along a plane, which is parallel to the object plane, via the operating movements. From the perspective of the viewer of the display unit, the displayed image section is shifted.

It is therefore conceivable to provide an input device with an input element that can be moved in different axes, wherein the movements (for example, translational movement along two or more axes, as well as rotational and/or pivot motion along two or more axes) are detected by suitable sensors and converted into control commands.

According to another exemplary embodiment of the handling device, the control device aligns the two or more movement axes of the input device with the present orientation of the image capturing unit, so that operating movements of an input element of the input device result in movements of the displayed image section in the same direction. This ensures that the operator can intuitively control the desired movements by moving left, right, up/front or down/back. The operator does not need to be concerned about the coordinate transformation. This is done by the control device.

In other words, a pivot motion to the right can cause the observation instrument to move to the right along the curved surface while maintaining the object distance and the centering of the image capturing unit. Similarly, a pivot motion to the left causes the observation instrument to move to the left along the curved surface. Furthermore, a linear movement to the right, for example, can cause the observation instrument to move to the right along the plane parallel to the object plane. Similarly, a linear movement to the left causes a movement of the observation instrument to the left along the parallel plane. The object distance in relation to the object plane remains the same.

According to another exemplary embodiment of the handling device, the input device is arranged as a single-handed input device, wherein the input device detects operating movements at least in the form of a rotation around a longitudinal axis or a translation along the longitudinal axis in order to detect movement signals for controlling a zoom function and for a focus adjustment. Accordingly, the input device can fulfill further functions. In a simple manner, a plurality of functions (movement, magnification, etc.) can be controlled in only one operating mode. However, it is also conceivable to provide different operating modes to allow unambiguous controlling.

According to a further exemplary embodiment of the handling device, the control device is adapted to perform an initialization procedure in order to acquire configuration information relating to the supported observation instrument, wherein the initialization for instance comprises a query via the instrument control unit, and wherein the configuration information is transmitted to the handling control unit and taken into account for the control of the handling unit.

In this way, the control device can determine what type of observation instrument is currently attached to the robotic handling unit, by way of example. The observation instrument type involves, for example, its dimensions, parameters of its image capturing unit, the ability to exchange data, a possible rotational position for turning the image capturing unit, and a possible sensor for detecting the rotational position of the image capturing unit, etc.

The term initialization procedure should not be understood to mean that it is merely a one-time procedure. The initialization procedure can be executed repeatedly, for example, for each specific treatment or diagnostic task, for example, when the control device is started up or when the handling device is changed. The initialization procedure can also be repeated in a targeted and automated manner, for example, by periodic repetitions. Conversely, it is conceivable that the operator can consciously trigger the initialization procedure.

In other words, for instance, during the initialization procedure a certain offset can be determined, wherein the control device (handling control unit) for the robotic handling unit uses this offset for controlling the robotic handling unit. This offset defines, for example, the position of the image capturing unit in relation to the elements of the handling unit. The offset may describe the geometric shape/extension of the observation instrument. In this way, the image capturing unit of the observation instrument can be precisely controlled to move the image section as desired.

By way of example, it is conceivable to start the query that is part of the initialization procedure by pressing the enabling switch to activate the second operating mode. The initialization procedure can also be referred to as a setup procedure. Accordingly, it is conceivable to use different camera systems/observation instruments. The data (configuration information) can be provided directly by the observation instrument. Alternatively, the observation instrument can be identified by its ID, which can be used to query data from a database.

According to a further exemplary embodiment of the handling device, the control device is adapted to mirror the displayed image section upon request, wherein the implementation of operating commands at the input device takes the mirroring into account. In this way, a flip mode can be provided.

For example, a mirror image is created around a horizontal or vertical axis. This can happen, for example, when another operator takes over the control of the handling unit, who is standing on an opposite side of the patient from the view of the previously active operator.

In regard of the control method, the above and other objects are achieved by a method for controlling a handling device, the handling device comprising a robotic handling unit with an instrument holder, and an instrument mounted thereon and having an image capturing unit for capturing an image section of an object plane, the method comprising the steps of:

providing the instrument on the instrument holder,
controlling the instrument and the robotic handling unit via a control device, wherein the controlling takes place using an input device,
wherein the input device is operable in a first operating mode for controlling the instrument and in a second operating mode for controlling the robotic handling unit, and
activating the second operating mode, in which the robotic handling unit can be moved in response to input commands at the input device, by actuating an enabling switch.

The object of the disclosure is also completely achieved in this way.

According to a further exemplary embodiment of the method, the enabling switch can be operated in a first state 0, a second state I and a third state II depending of an applied actuating force, the second state I being an activation state for the second operating mode, the second operating mode being deactivated in the first state 0 and the second operating mode being deactivated in the third state II, and the second state I being interposed between the first state 0 and the third state II, when the enabling switch is switched.

It is conceivable to use the method for controlling a medical handling device. It is conceivable to use the method for surgical and/or diagnostic processes. However, it is also conceivable to use the method for processes other than surgical and/or diagnostic processes. Consequently, exemplary embodiments, in which the method is not used to perform a surgical/diagnostic procedure on the human or animal body, are also conceivable.

It is to be noted that the control method can be further refined corresponding to the exemplary embodiments of the handling device and vice versa. In other words, the subject matter of exemplary embodiments and further refinements related to the handling device may also become the object of corresponding embodiments of the method described herein.

It is to be understood that the above-mentioned features of the invention and those to be explained in the following can be applied not only in the respectively specified combination, but also in other combinations or singly, without departing from the scope of the present invention.

BRIEF DESCRIPTION OF THE DRAWINGS

Further features and advantages of the invention are disclosed by the following description of a plurality of exemplary embodiments, with reference to the drawings, wherein:

FIG. 3 is a schematic, simplified partial view of an image capturing unit on an observation head of an observation instrument and a display unit to illustrate an image orientation;

FIG. 4 is another representation analogous to FIG. 3 with a corrected image orientation by rotating the image capturing unit;

EMBODIMENTS

Figure 1:
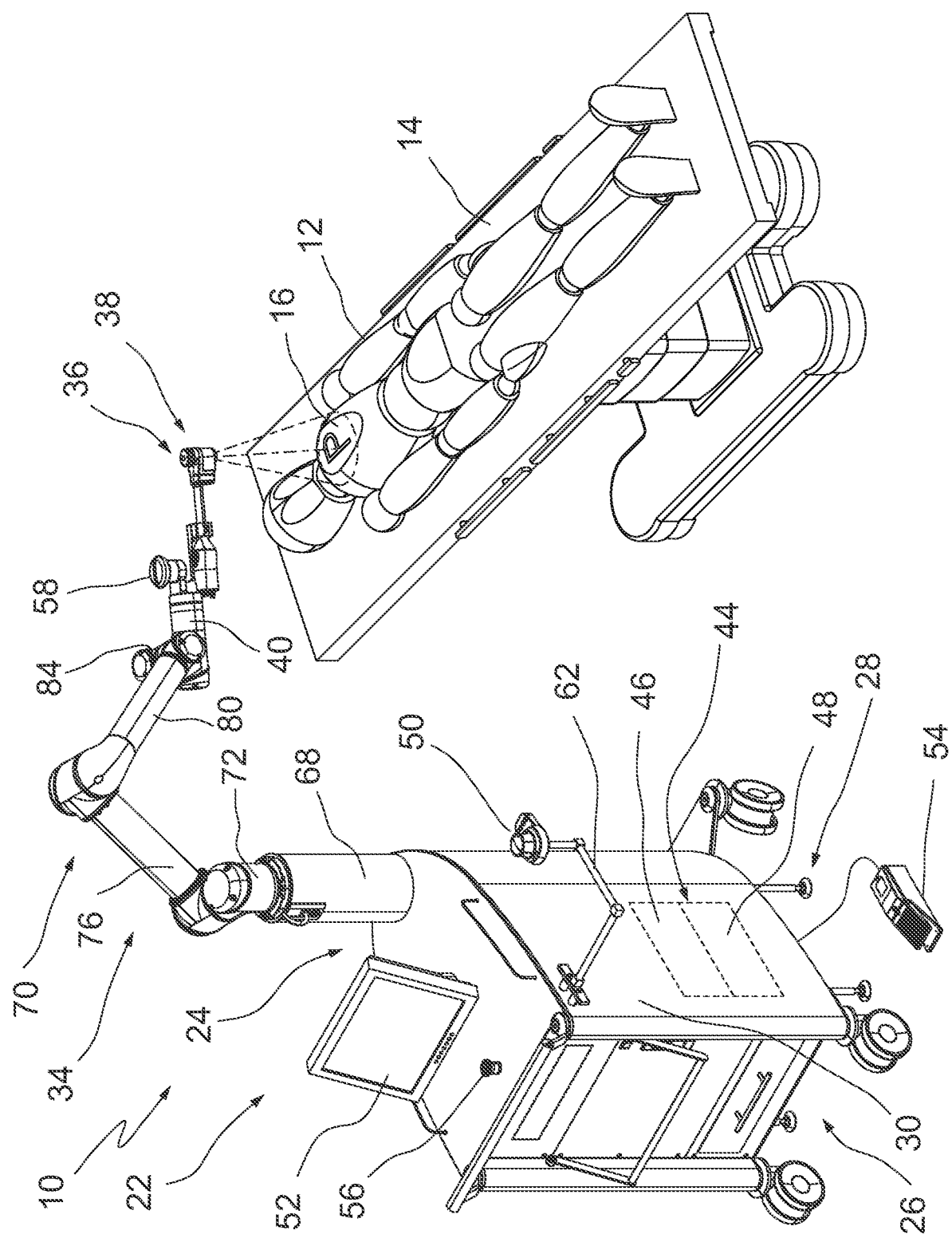
FIG. 1 is a perspective view of an embodiment of a medical handling device for observing an object field in a patient.

FIG. 1 shows a perspective overview of a handling device that is overall designated by 10. The handling device 10 can also be referred to as a medical handling device. In the embodiment shown in FIG. 1, the handling device 10 is assigned to a patient 12 who is placed on a table 14. The handling device 10 can be used for therapeutic, surgical and/or diagnostic purposes. However, its use for non-therapeutic, non-surgical and/or non-diagnostic purposes is also conceivable. This may include a use in exercises and/or simulations.

In the illustrated exemplary embodiment, the handling device 10 is used to observe an object field 16. The object field 16 is exemplarily a part of the patient's body 12. For illustrative purposes, the object field 16 is marked with the letter P in at least some of the figures shown herein. This is not to be understood to be limiting.

In the exemplary embodiment shown in FIG. 1, the object field 16 is located outside the body of patient 12. Accordingly, the handling device 10 in this exemplary embodiment serves to observe the body from outside the body. Alternative exemplary embodiments are conceivable, in which the handling device 10 can be used to observe the inside of the body, for example for endoscopic or laparoscopic observation.

In general, the handling device 10 is used for optical observation in the range of the visible electromagnetic spectrum and/or in adjacent peripheral areas. The main embodiments are therefore observations using white light, infrared radiation or UV radiation. Light that is visible to the human eye (white light) lies approximately in a spectral range between 380 nm and 780 nm. Radiation in the near-infrared range is in the range of about 780 nm to 1400 nm. So-called near UV light (also referred to as black light or UV-A light) is in the range of about 315 to 380 nm. So-called medium UV light (also referred to as UV-B light) is in the range of about 280 nm to 315 nm.

The above-mentioned areas can be used for white light observation as well as for PDD (photodynamic diagnostics) and PDT (photodynamic therapy) applications. This may also include fluorescence observation. In this context, fluorescence observation using indocyanine green (ICG) with fluorescence in the near infrared range is also conceivable.

The handling device 10 comprises a platform 22, which is arranged as a trolley or cart 24. This is not to be understood to be limiting. Nevertheless, at least in exemplary embodiments, a movable platform 22 is provided. This increases flexibility and suitability for various applications. Accordingly, the platform 22 is arranged as cart 24 with a chassis 26, for example. In the embodiment shown in FIG. 1, the cart 24 comprises not only a chassis 26 but also a so-called support 28 and/or a corresponding support unit.

The support 28 is used to protect the cart 24 against unintentional movement during operation of the handling device 10. Accordingly, the support 28 can be used to jack up the cart 24. As an alternative or in addition, it is intended to block the wheels of the chassis 26 in the sense of a parking brake. The status of the cart 24 (mobile or jacked up/locked) can be monitored by suitable sensors in order to enable operation of the handling device 10 only if it is ensured that the cart 24 cannot be moved unintentionally. It is understood that the cart 24 can also be anchored/fixed in other ways to enable safe operation of the handling device 10.

Furthermore, the platform 22 comprises a housing 30, which accommodates elements/units of the handling device 10. This results in a compact, clear design. In addition, the handling device 10 is easier to clean, and can also be arranged as a shelf or shelf trolley. In exemplary embodiments, essential control units for the handling device 10 are arranged in the housing 30 of the cart 24. This means that the platform 22 is mobile, so that use at different locations and/or in different rooms is conceivable. It is understood that the platform 22 and/or the cart 24 are nevertheless coupled with the environment, for example for energy supply, signal supply and/or media supply purposes.

The platform 22 or the cart 24 forming the platform supports a handling unit 34. In the illustrated exemplary embodiments, the handling unit 34 is arranged as a motorized handling unit, for example as a robotic handling unit. Alternatively, the handling unit 34 can be referred to as a telemanipulator unit. Accordingly, the platform 22 forms a base for the handling unit 34. At least in the embodiments shown herein, control devices for the handling unit 34 are located on the platform 22 and/or in its housing 30.

The handling unit 34 is adapted to carry/hold an instrument 36. The instrument 36 can be moved by motor via the handling unit 34. Accordingly, the handling unit 34 can be referred to as a telemanipulator for instrument 36. The instrument 36, for example, is a medical instrument. At least in exemplary embodiments the instrument 36 is arranged as observation instrument 38. The observation instrument 38 is, for example, an instrument for observing the patient from outside the body, i.e. at a distance from the patient's body. Such an observation instrument 38 can be arranged and referred to as an exoscope. However, it is also conceivable to design the observation instrument 38 as an instrument for observing the inside of the patient's body, for example as a laparoscope or endoscope.

The instrument 36 is mounted on an instrument holder 40. For instance, the instrument 36 is detachably mounted on the instrument holder 40. In other words, the instrument 36 can also be detached from the instrument holder and therefore from the handling unit 34. It is therefore conceivable to use the instrument 36 in alternative applications as a hand-guided/hand-held unit. For illustrative purposes, it is assumed in the following that the instrument 36 is used as an observation instrument 38 for observing an object field 16, for instance as a medical observation instrument 38 for observing an object field 16 in a patient 12.

In FIG. 1, the reference sign 44 illustrates a control device 44, which is mounted on platform 22, by means of dashed lines. By way of example, platform 22 comprises a cart 24 with a rack that includes an enclosure in the form of a housing 30. Accordingly, the control device 44 can be accommodated and held on this rack.

At least in exemplary embodiments, the control device 44 comprises a handling control unit 46 and an instrument control unit 48. The handling control unit 46 and the instrument control unit 48 can be discrete, basically separate control units/control modules. In other words, several units can be combined to form the control device 44. However, it is also conceivable to form the control device 44 in such a way that the handling control unit 46 and the instrument control unit 48 at least partially use common hardware/computer technology. In other words, it is conceivable to design the handling control units 46, 48 discretely and/or integrally. Mixed forms are conceivable.

For controlling the handling device 10 and, in certain embodiments, for interaction with the control device 44, various input devices are provided for an operator (e.g. a surgeon or an assistant). For example, an input device 50 is provided, which is arranged as a single-handed input device. For example, the input device 50 is arranged as a so-called 3D mouse, at least similar to a 3D mouse. In other words, the input device 50 can be adapted to detect user inputs and consequently control commands in several spatial axes, where the input is made by only one hand, acting on a single input element. The input device 50 is for instance used for controlling the robotic handling unit 34 as well as for controlling the observation instrument 38 and/or for controlling a reproduction of an image captured by the observation instrument 38. In this context, reference is again made to US 2017/0163972 A1, which discloses the use of a single-handed input device for controlling imaging parameters and for controlling image reproduction parameters.

Another input device 52 is arranged as a so-called touch monitor. Accordingly, the input device 52 can be used for selection decisions, general settings and similar functions. Basically, it is also possible to control the robotic handling unit 34 via the input device 52. The input device 52, arranged as a touch monitor, can be used, for example, to make general settings with regard to the instrument 36 (observation instrument 38). Furthermore, operating parameters for the operation of the observation instrument 38 can be selected and/or entered via the input device 52.

Another input device 54 is arranged as a foot switch, for instance. The footswitch can be operated by the operator without the need for hands. The input device 54 arranged as a foot switch can be used for instance as an enabling switch. The design as a foot switch is not to be understood to be limiting.

Basically, the input device 54 is intended to enable certain functions/operations when required, and only on the explicit command of the operator. In other words, the input device can be used to prevent certain functions from being triggered unconsciously. In this way, for instance the robotic handling unit 34 can be operated safely. This relates for instance to movements of the instrument holder 40 (with the instrument 36 mounted thereon) in relation to the patient 12 or the table 14. Such movements should be possible if there is an additional release signal via the input device 54. Furthermore, the input device 54, which serves as an enabling switch, can be coupled with a safety control (enable control).

Furthermore, the embodiment of the handling device 10 illustrated in FIG. 1 illustrates a further input device 56, which is arranged as a button or push-button. The input device 56 may basically be arranged as an emergency stop button. Accordingly, the input device 56 can cancel a current action of the handling device 10, for instance of the robotic handling unit 34. However, it is also conceivable that the input device 56, similar to the input device 54 described above, can be used as an enabling switch for activating (enabling) certain functions. Both embodiments increase the safety when operating the handling device 10.

In the embodiment of the handling device 10 illustrated in FIG. 1, a further input device 58 is provided directly on the robotic handling unit 34. The input device 58 is located on or near the instrument holder 40. The input device 58 is used in a so-called direct control mode for quasi-direct control/displacement of the handling unit 34 and consequently of the observation instrument 38. In other words, the operator can quasi-manually control the observation instrument 38 in the direct control mode (also referred to as direct drag mode) by simply dragging and/or pivoting/rotating the input device 58, which is designed, for example, like a handle, mushroom-shaped or button-shaped.

In the direct control mode, the handling unit 34 is operated by the control device 44 and/or by its handling control unit 46 in such a way that the robotic handling unit 34 immediately follows the operating commands. This gives the operator the impression that the observation instrument 38 can be maneuvered in space directly or almost directly. The handling unit 34 follows the movement, i.e. the control command, of the operator. If the control movement by the operator ends, the handling unit 34 remains in the currently selected position and holds this position and thus also the observation instrument 34 in space. In the direct control mode, the handling unit 34 can be controlled in such a way that a defined force must be overcome by the operator when directly acting on the input device 58.

In an exemplary embodiment, the input device 50 is connected to platform 22 via a boom 62. The boom 62 can have different links, which are adjustable. Therefore, depending on the situation, an ergonomically favorable position for the input device 50 can be set. For instance, the input devices 50, 52, 54, 56, 58 are directly or indirectly coupled to the control device 44 in terms of signaling (e.g. via data lines or radio). This can include a coupling with the handling control unit 46 and/or the instrument control unit 48.

Figure 2:
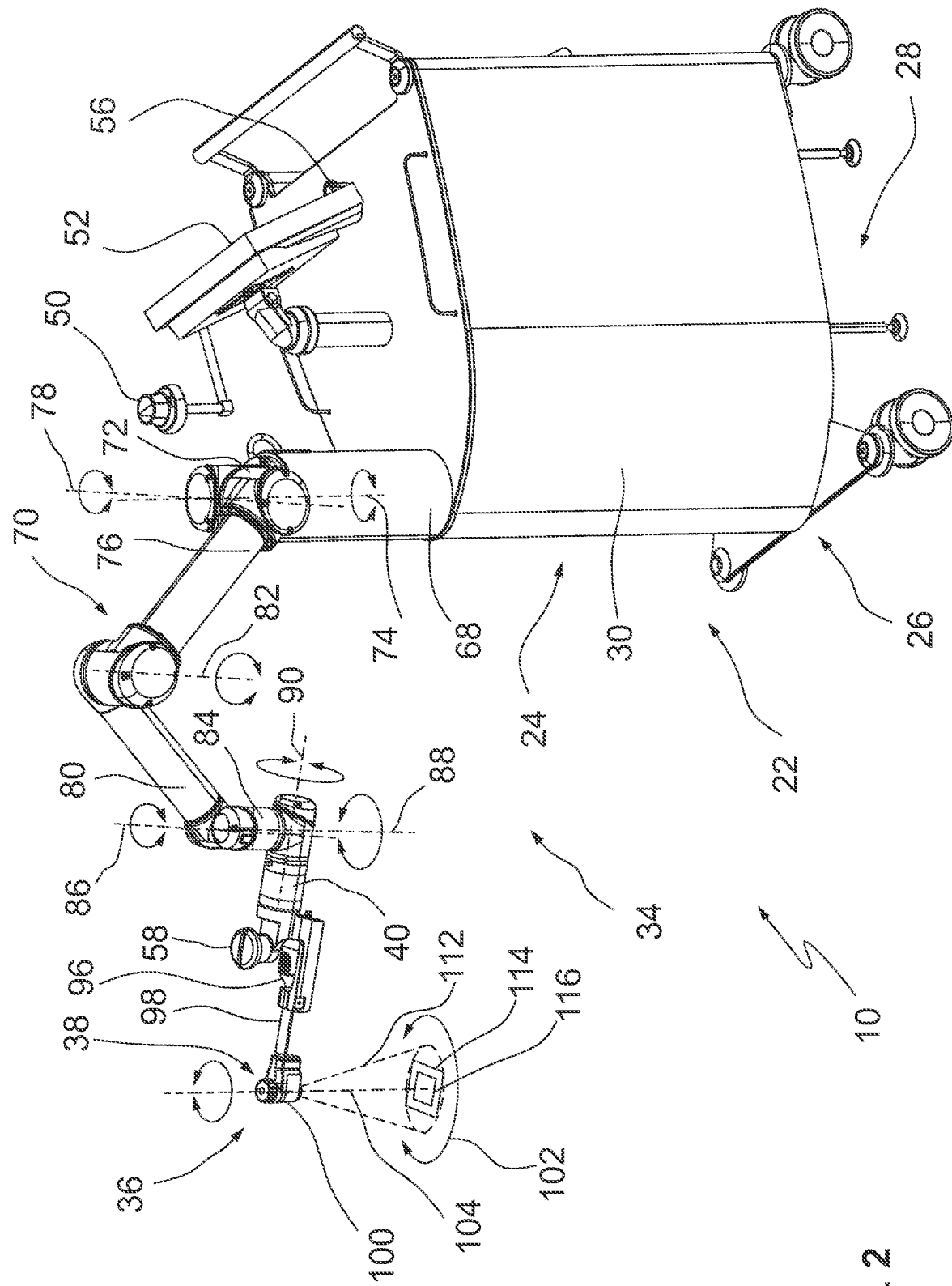
FIG. 2 is another perspective view of the handling device according to FIG. 1 in a different view orientation.

FIG. 1 and FIG. 2 illustrate an exemplary embodiment of the robotic handling unit 34. The handling unit 34 comprises a base frame 68, which is arranged on the platform 22, which is arranged as cart 24. In other words, the handling unit 34 can be moved at least in the exemplary embodiment shown in FIG. 1 and FIG. 2.

The handling unit 34 comprises a kinematic chain 70, the base of which is formed by the base frame 68 on the platform 22. The handling unit 34 is arranged as an open kinematic chain. In other words, the kinematic chain 70 comprises a number of links, which are arranged in a row and coupled to one another.

The handling unit 34 comprises a carousel 72, which is mounted on the base frame 68. The carousel 72 can be rotated (about a vertical axis) in relation to the base frame 68. Accordingly, a joint 74 is provided between the carousel 72 and the base frame 68. The joint 74 defines an axis of rotation (in the exemplary embodiment vertical axis). The base frame 68 forms a proximal end of the kinematic chain 70 of the handling device 34. The instrument holder 40 forms a distal end of the kinematic chain 70 of the handling device 34.

The carousel 72 is connected to a swing arm 76, which is coupled to the carousel 72 via a joint 78, cf. FIG. 2. The joint 78 defines an axis of rotation (in the exemplary embodiment horizontal axis). Furthermore an arm 80 is provided, which is coupled with the swing arm 76 via a joint 82. The joint 82 defines an axis of rotation. In the kinematic chain 70, an element referred to as hand 84 follows, which is coupled to the arm 80 via a joint 86 (cf. FIG. 2). The joint 86 defines an axis of rotation.

The element referred to as hand 84 is followed in the exemplary embodiment according to FIGS. 1 and 2 by the instrument holder 40 for supporting the observation instrument 38. The instrument holder 40 is coupled to the element referred to as hand 84 via a joint 88. Joint 88 defines a pivot axis. The instrument holder 40 can be rotated about the axis defined by joint 88 relative to the hand 84 and/or relative to the arm 80. It is also conceivable that the instrument holder 40 can be rotated about its longitudinal axis, cf. joint 90, which also defines a rotation axis. The illustration in FIG. 2 is not to be understood to be limiting.

In an exemplary embodiment, the joints 74, 78, 82, 86, 88, 90 are each assigned with a drive. The drive is for example a direct drive or servo drives. The drives are not explicitly shown in FIG. 2.

It is understood that the design of the handling unit 34 may also differ from the embodiment shown in FIGS. 1 and 2. This relates, for example, to the number of links in the kinematic chain 70 and/or the actual degrees of freedom and/or movement axes between adjacent links. Basically, the robotic handling unit 34 can be used to move the observation instrument 38 in at least two degrees of freedom relative to the patient 12 and/or the table 14. For instance, the handling unit 34 allows the observation instrument 38 to be moved in four, five, six or even seven degrees of freedom. It is to be noted that robotic handling units with more or less links and also with different degrees of freedom of movement may also be used. The number of movable (usually pivoting) axes is usually selected so that the desired degrees of freedom can be provided for the instrument 36.

FIGS. 3 and 4 illustrate by means of simplified schematic representations an exemplary embodiment of an observation head of the observation instrument 38, which is designated by 100, cf. also FIG. 2. The observation instrument 38 comprises a housing 96. A shaft 98 extends from the housing 96 towards a distal end of the observation instrument 38. The observation head 100 is located at the distal end. FIGS. 3 and 4 illustrate only the distal end of the observation instrument 38 with the processing head 100.

In FIG. 3 and FIG. 4, it can also be seen that at least in exemplary embodiments a rotational degree of freedom (cf. double arrow 102) is provided for the observation head 100 and/or for an image capturing unit installed therein. Accordingly, an image erection (image rotation) with respect to an optical axis 104 is possible, cf. also FIG. 2. The observation instrument 38 with the observation head 100 is adapted to observe a field of view 112 (cf. FIG. 2 and FIG. 5) and to capture an image section 116 in a recording area 114 in the field of view 112. This is done in an object plane and/or object field 16 (cf. FIG. 1). The field of view 112 is defined by an optical imaging system of the observation head 100.

The field of view 112 and image sensors (one or more sensors) installed in the observation head 100 define the (possible) recording area 114, which cannot be larger than the field of view 112. The recording area 114 is defined by the size of one or more image sensors and the imaging optics. The image section 116 can basically correspond to the recording area 114. However, it is also conceivable, at least in exemplary operating modes, that the image section 116 is deliberately chosen smaller than the recording area 114. On the one hand, this is conceivable for a digital zoom feature. Furthermore, the image section 116 can be selected smaller than the recording area 114 in order to avoid or at least minimize any imaging errors/display errors in the edge area of the recording area 114 (i.e. at the edges of the image sensors).

The observation instrument 38 comprises an image capturing unit 118 for capturing the image section 116 and/or the recording area 114. The embodiment shown in FIGS. 3 and 4 involves a stereo image capturing unit 118. Accordingly, the image capturing unit 118 comprises a first sensor 120 and a second sensor 122. The sensors 120, 122 are arranged as CCD image sensors, CMOS image sensors or similar. The sensors 120, 122 each have a plurality of detecting pixels. It is understood that the image capturing unit 118 can also be arranged as a (mono) image capturing unit with only one observation channel. The reference signs 124 each indicate a center and/or a center point of the sensors 120, 122.

A display unit 128 is provided for reproducing the captured image. The display unit 128 includes a monitor or a similar display. The display unit 128 is designed in exemplary embodiments for stereoscopic image reproduction. Accordingly, the display unit 128 can be arranged as a 3D monitor. Designs are conceivable, in which a monitor is viewed through auxiliary means (3D glasses) in order to achieve the stereoscopic effect. However, designs are also conceivable, in which the display unit 128 is arranged as a head-mounted display (HMD), for example as video glasses.

A stereo image capturing unit 118 enables stereoscopic observation, if necessary even 3D observation. This is made possible by an offset between the two sensors 120, 122, which is adapted to the offset between the right and left eye of the observer. In this way, a spatial impression is obtained during observation. However, stereoscopic observation requires that the two sensors 120, 122 are aligned in a certain way, namely along an (artificial) horizon 140, which is adapted to the position of the display unit 128 and indirectly to the position of the eyes and/or the eye area of the observer.

In the state illustrated in FIG. 3, the display unit 128 shows an image section 130 in a first orientation, which results from the orientation of the image capturing unit 118 in relation to the observation head 100 and, overall, from the orientation of the observation instrument 38 in relation to the object field 16 at the patient 12. The representation of the image section 130 in FIG. 3 illustrates an inclined orientation with reference to an example (letter P), in which the immediate understanding and for instance the assignment of directions is difficult for the observer. It would be desirable for the observer to use the orientation of image section 132 shown in FIG. 4. The orientation of the image section 130 in FIG. 3 results from the present orientation of the image capturing unit 118, cf. the horizon 140.

In order to align the displayed image section 132 in the desired way, it is necessary to rotate the image capturing unit 118 with the sensors 120, 122, cf. the orientation of the horizon 140 of the image capturing unit 118 in FIG. 4. For this purpose, the rotational degree of freedom 102 is provided, which enables image erection. The image erection using the rotatability of the image capturing unit 118 around the optical axis 104 with respect to the observation head 100 is in certain embodiments potentially advantageous for stereo image capturing units. However, there may also be benefits for mono image capturing units 118 with only one observation channel, for example with respect to given dimensions (for example an aspect ratio) of the image sensor used.

In an exemplary embodiment, the observation head 100 comprises a position sensor/orientation sensor 142 for detecting a rotational position of the image capturing unit 118 in relation to the observation head 100 and/or the shaft 98 of the observation instrument 38. Based thereon, a desired orientation of the image section 130, 132 can be set, depending on the actual orientation of the image capturing unit 118.

It is basically conceivable to manually rotate the image capturing unit 118 around its optical axis 104. In alternative embodiments, it is also conceivable to use a drive 144 to rotate the image capturing unit 118 around the optical axis 104. If a drive 144 is used, the orientation sensor 142 can be integrated into the drive 144. However, it is also conceivable to derive the rotational position/orientation of the image capturing unit 118 from control data for controlling the drive 144. Thus, if a certain rotational increment is given to the drive 144 for a rotational movement, then, conversely, at least the target orientation of the image capturing unit 118 is known.

It is understood that an electronic/digital image erection is also conceivable, wherein the image section that is captured and displayed is digitally rotated. However, such feature is hardly realizable in the case of stereo observation while maintaining the stereo functionality. However, in exemplary embodiments a digital fine adjustment or fine alignment is conceivable.

It is understood that, in principle, the observation instrument 38 could also be aligned via the robotic handling unit 34 in order to align the displayed image section 130, 132. However, this would often have the result that the observation instrument 38 and/or the handling unit 34 get in the way and could impair the free direct view of the operating field/object field for the surgeon and/or third parties. Furthermore, in many cases the operating field must be accessible for other instruments. For this reason, the robotic handling unit 34 is generally aligned in such a way that it disturbs the workflow as little as possible. In this case, however, the image capturing unit 118 may have to be rotated using the degree of freedom 102 in order to erect the image in the desired way.

However, this alignment/erection by rotation of the image capturing unit 118 may result in the robotic handling unit 34 not being able to be controlled intuitively. For example, if the observer/operator uses the input device 50 to give control commands in the form of direction commands and travel commands to move the observation instrument 38 via the handling unit 34, he regularly orients himself towards the displayed image section 116 (cf. Also reference signs 130, 132 in FIGS. 3 and 4). However, the orientation of the scene in image section 116 often does not correlate with the actuation axes (for example right-left-front-back) of the input device 50. In such a case, a movement to the right at the input device 50 does not necessarily lead to a corresponding movement of the displayed image section 116 to the right.

FIG. 3 and FIG. 4 further illustrate an exemplary embodiment where the displayed image and/or the displayed image section 116, 132 is smaller than the theoretically available recording range 114 of the sensors 120, 122. Thus, if only a section of the respective recording area 114 is displayed, it is theoretically possible to displace the displayed image section 116 within the recording area 114. This is indicated in FIG. 4 by a shifted image section 134 and a coordinate system marked 136. Furthermore, this allows, as already indicated before, a so-called digital zoom, at least within certain limits.

The orientation of the image section 114 in FIG. 3 (in relation to the image section 116, 130 displayed by the display unit 128) illustrates that a larger image section 114 is also potentially advantageous for digital image rotation. Thus, the displayed image section 116, 130 can be rotated at the given aspect ratio and/or generally at the given shape of the display unit 128 without omissions in the corners of the display unit 128, for example.

The ability to select the image section 116, 132 smaller than the recording area 114 leads to situations where a current center and/or center of the displayed image section 116, 132 does not correspond to the center 124 of the sensor 120, 122. This must be taken into account when operating the handling device 10.

In accordance with an aspect of the present disclosure, it is proposed to interpose a coordinate transformation in order to allow intuitive control of the handling unit 34 for the movement of instrument 36 and/or observation instrument 38. This approach makes it possible, for example, to use the displayed image section 116 as a basis for controlling, for instance its orientation.

Figure 5:
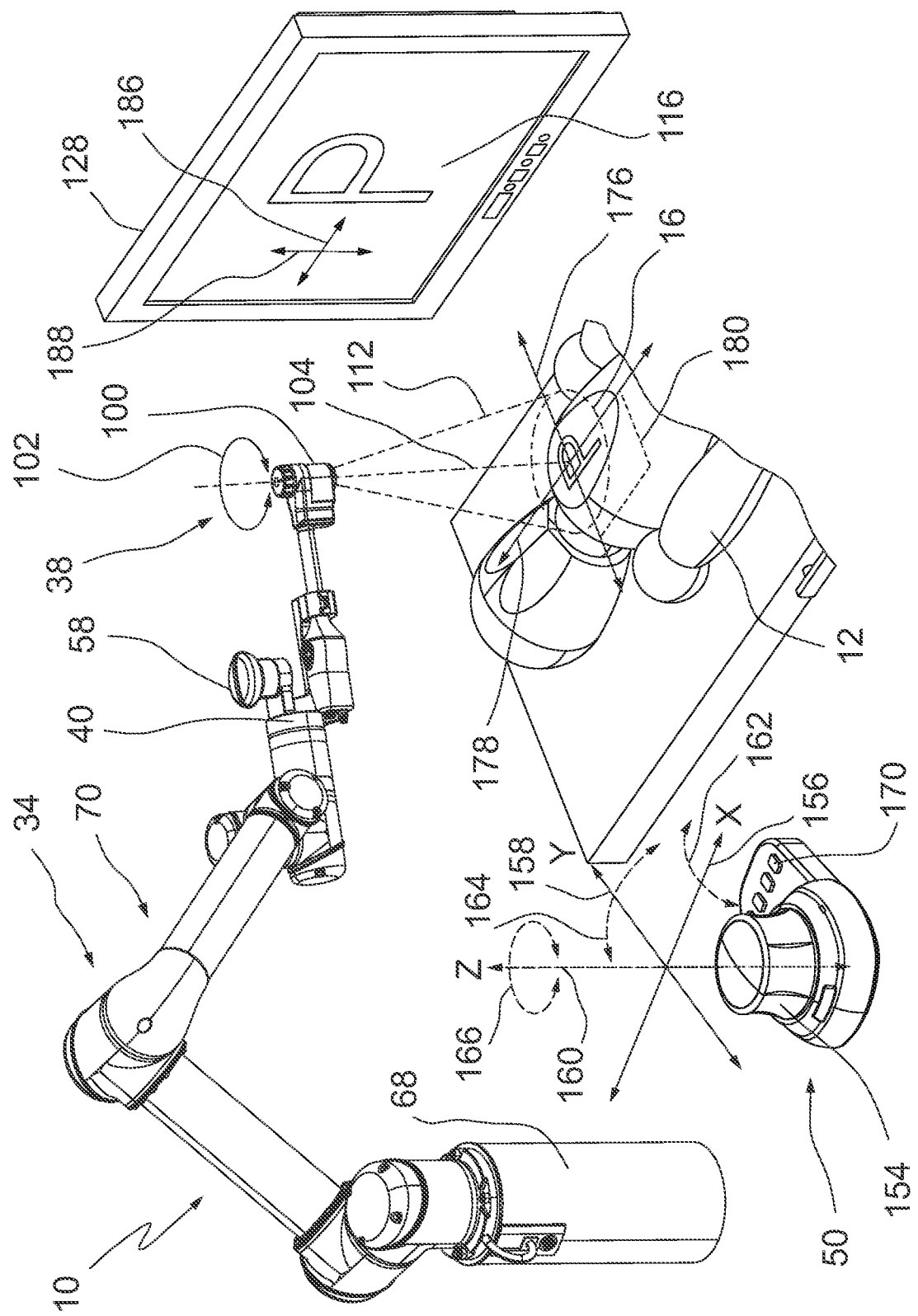
FIG. 5 is a partial perspective view of an embodiment of a handling device with an observation instrument to illustrate an exemplary function of the handling device.

This is illustrated with additional reference to FIG. 5. FIG. 5 shows a state, in which the image capturing unit (not explicitly shown) in the observation head 100 of the observation instrument 38 is aligned around the optical axis 104 in such a way that the image section 116 shown in the display unit 128 is shown in the desired orientation. This orientation is now the basis for controlling the robotic handling unit 34.

The control of the handling unit 34 is carried out, for example, via an actuating element 154 of the input device 50. By way of example, the actuating element 154 is designed button-like, plate-like or puck-like. However, the actuating element 154 can also be designed similar to a joystick. Alternatively, the actuating element 154 can be designed similar to a so-called rotary pushbutton. The actuating element 154 comprises different movement axes and/or input axes. Control commands can be generated via these input axes by the operator acting on the actuating element 154 in the desired way. For instance, the actuating element 154 is arranged as a multi-axis actuating element. Accordingly, the actuating element 154 is designed, for example, to detect movements along several linear axes 156, 158, 160.

A total of six degrees of freedom are conceivable, for instance three translational and three rotational degrees of freedom.

By way of example, the axis 156 can be referred to as a translation axis. The axis 156 is exemplarily assigned to an X-direction. A travel motion/linear movement can be induced along the axis 156. It is understood that the actuating element 154 can only be deflected to a small extent along the axis 156. By way of example, the axis 158 can be referred to as a translation axis. The axis 158 is assigned to a Y direction, by way of example. A travel motion/linear movement can be induced along the axis 158. It is understood that the actuating element 154 can only be deflected to a small extent along the axis 158. By way of example, the axis 160 can be referred to as a lift axis. The axis 160 is assigned to a Z direction, by way of example. A travel motion/linear movement can be induced along the axis 160. It is understood that the actuating element 154 may only be deflected to a small extent along the axis 160.

In other words, translational movements of the observation head 100 of the observation instrument 38 in a plane (approximately an X-Y plane) can be caused by slight movements of the actuating element 154 along the axes 156, 158.

The lift axis 160 can be used, for example, to change an object distance (reference mark 196 in FIG. 6 and FIG. 7) between the observation instrument 38 and the object field 16. Basically, it is also conceivable to use a movement along the lift axis 160 (Z direction) for controlling a focus drive.

In addition, the actuating element 154 according to the embodiment as shown in FIG. 5 comprises pivot axes and/or rotation axes 162, 164, 166. The pivot axis 162 describes pivot motions around the axis 156, for example around the X-axis. The pivot axis 164 describes pivot motions about axis 158, for example about the Y-axis. The pivot axis or rotation axis 166 describes pivot motions/rotational movements about axis 160, for example, about the Z-axis.

The pivot axes 162, 164 can be used, for example, to tilt observation instrument 38, which is mounted on the robotic handling unit 34, with respect to the object field 16. This is done by controlling the handling unit 34 in reaction to pivot motions about the pivot axes 162, 164, which the operator performs on the actuating element 154. In an exemplary embodiment, the observation instrument 38 is pivoted around the focus point, i.e. the set working distance (pivot motion).

The rotation axis 166 can be used, for example, to control a focus drive of the observation instrument 38. Basically, it is also conceivable to change the working distance/object distance (reference sign 196 in FIG. 6 and FIG. 7) between the observation instrument 38 and the object field 16 in response to user inputs (rotational movements). It is possible to switch between these operating types by using an enabling switch. By way of example, axis 160 is used for changing the working distance and axis 166 for controlling the focus drive. Conversely, it is conceivable to use axis 160 for controlling the focus drive and axis 166 for changing the working distance.

In principle, it is conceivable to form the actuating element 154 to be deflectable in several spatial directions. In this way, a clear operation is achieved for the operator. However, it is also conceivable to detect the effect of a force on the actuating element 154, for example by means of suitable force sensors. In such a case, the actuating element 154 is not necessarily macroscopically deflectable. Instead, it has a microscopic deflectability. In this way, movements can also be detected and assigned to axes 156, 158, 160, 162, 164, 166 and, on this basis, converted into control commands.

The input device 50 has, for example, further actuating elements 170 in the form of buttons or knobs. In this way, further functions can be controlled. For instance, certain commands can be acknowledged. Furthermore, a selection of a current operating mode of the input device 50 via one of the actuating elements 170 is conceivable. Another possible use for the actuating elements is a storing of current positions of the handling unit 34 and/or the observation instrument 38, wherein the stored position can be approached from a position that has been assumed in the meantime. Both the storing of a position and the moving to a previously stored position can be effected by the operating elements 170. Moving to the previously stored position can be limited to the target position. Alternatively, the previously stored position can be approached in such a way that the previously used movement path is traversed "backwards".

In accordance with the example configuration illustrated in FIG. 5, a coordinate transformation and/or an alignment of the orientations/coordinate systems is performed to simplify controlling.

In FIG. 5, double arrows 176, 178 that are projected into the object field 16 illustrate a coordinate system that reflects the orientation of the image capturing unit. Accordingly, in the operating mode shown in FIG. 5, it is desired to move the observation instrument 38 and consequently the object field 16 in a plane 180 in response to operating commands at the input device 50. Such a movement in the plane 180 is achieved by interpolation and corresponding controlling of the links of the kinematic chain 70 of the robotic handling unit 34.

In the image section 116 shown on the display unit 128, the resulting movement axes 186, 188 are indicated. In the illustrated exemplary operating mode, axis 156 at the input device 50 is assigned to the resulting axis 186. Furthermore, the axis 158 at input device 50 is assigned to the resulting axis 188 in image section 116. Accordingly, the robotic handling unit 34 is controlled in such a way that the displayed image section 116 is moved to the right or to the left when the input element 154 is moved to the right or to the left. Furthermore, the robotic handling unit 34 is controlled in such a way that the displayed image section 116 is moved up or down along the indicated axis 188 when the input element 154 is moved back and forth. Such an operation is intuitive and can be carried out while observing the displayed image section 116 on the display unit 128.

However, this operating mode requires the detection of a current orientation (curved double arrow 102) of the image capturing unit in the observation head 100 and a consideration of this alignment (cf. double arrows 176, 178) in the control of the robotic handling unit 34, for instance when using a stereo image capturing unit 118 (cf. FIG. 2 and FIG. 3). In FIG. 5, for example, the horizon 140 of the image capturing unit 118 (cf. again FIG. 2 and FIG. 3, also cf. the double arrow 176 in FIG. 5) is aligned parallel to the interpolated axis 176. This alignment is taken into account when interpolating the trajectories for the desired X-Y movements in the plane 180. In other words, when implementing operating commands at the input device 50, the coordinate transformation is for instance carried out in such a way that axes 156, 176, 186 are aligned parallel to each other in respect of the control commands to the handling unit 34, and that axes 158, 178, 188 are aligned parallel to each other in respect of the control commands to the handling unit 34. Then, the displayed image section 116 can be easily moved in the 180 plane.

The operator can therefore orientate himself independently of the external orientation/position of the handling unit 34 and/or the observation instrument 38 by the orientation of the image section 116 on the display of the display unit 128, in order to control the image section 116 intuitively in at least two axes via user inputs on the assigned input axes 156, 158 of the input device 50.

At least in exemplary embodiments, other degrees of freedom of the actuating element 154 of the input device 50 are not taken into account during this specific travel mode, so that an ideal or almost ideal movement in plane 180 is possible.

Of course, other modes of operation are also conceivable, such as a spatial mode or 3D mode, in which the input device 50 can be used to control/move the observation instrument 38 in three or more spatial axes (translation axes/linear axes and pivot axes/rotation axes).

FIG. 5 illustrates a mode, in which the observation instrument 38 is moved as parallel as possible with a constant distance to the observed object field 16. The object distance (cf. again the reference sign 196 in FIG. 6 and FIG. 7) remains essentially the same.

Figure 6:
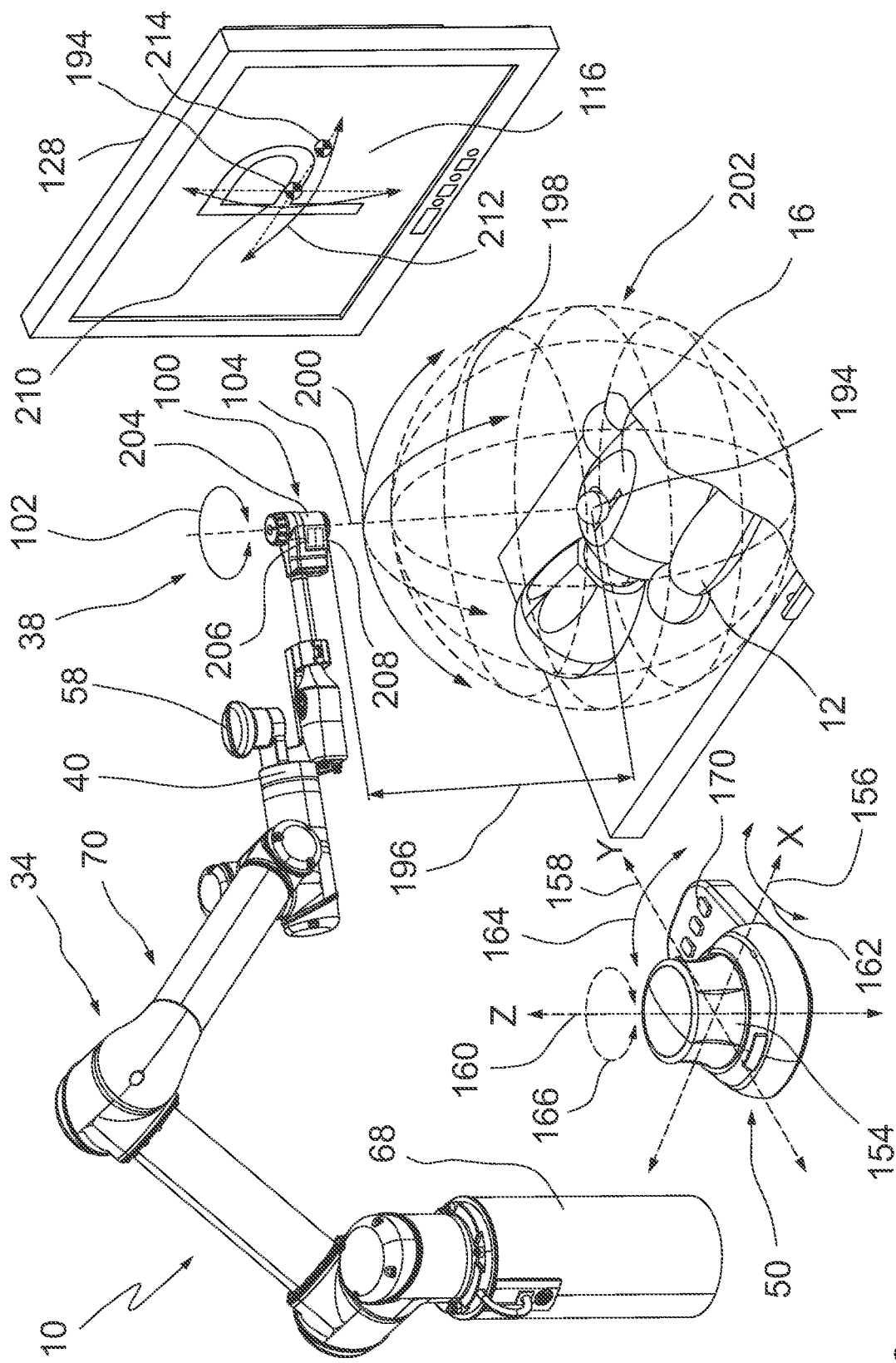
FIG. 6 is another partial perspective view of an embodiment of a handling device with an observation instrument to illustrate another exemplary function.

In addition, FIG. 6 illustrates another mode, in which the observation instrument 38 is moved along a curved path or surface/shell with respect to a pivot point 194 in the object field 16. By way of example, the pivot point 194 is a center of the image section 116, which represents a part of the object field 16. The movement along the curved shell (for example a spherical shell or a spherical half shell) is carried out at least in exemplary embodiments under consideration of a constant object distance 196.

In other words, the movement of the observation instrument 38 can be along interpolated curved axes 198, 200, which are assigned to a spherical surface 202 (sphere or spherical segment). By way of example, and not to be understood to be limiting, the axis 198 is associated with a 0° longitude and the axis 200 with a 90° longitude. The movement along/on the spherical surface 202 is performed while maintaining an alignment with the optical axis 104 to the selected pivot point 194, which can be derived from a current center of the observed image section 116. However, the pivot point 194 can also be located and selected off-center in the image section 116. The pivot point 194 can basically also be referred to as a focus point.

In an exemplary embodiment, the observation instrument 38 comprises observation optics 204 at observation head 100. By way of example, a focus drive 206 is assigned to the observation optics 204 for focus adjustment. The focus drive 206 is used to adjust a focus distance of the observation optics 204 to the selected working distance/object distance 196 so that the currently observed object field 16 is imaged sufficiently sharply. The focus drive 206 can be controlled manually and/or automatically.

At least in exemplary embodiments, the observation instrument 38 also comprises a measuring device 208 for determining the object distance 196. In this way, the current object distance 196 can be determined. During the movement of the observation instrument 38 along the curved path and/or surface 202 illustrated in FIG. 6, the object distance 196 is to be kept constant. For this, however, the object distance 196 must first be determined, at least in some of the embodiments. This is done by the measuring device 208.

In an alternative embodiment, the control device 44 may determine the object distance 196 indirectly via current operating parameters of the observation optics 204 and/or the focus drive 206. In other words, a certain state of the observation optics 204 indicates a certain object distance 196.

By way of example, controlling the movement along the curved axes 198, 200 is done using the pivot axes 162, 164 of the input device 50. In other words, for example, pivoting the actuating element 154 about the X-axis 156 (pivot axis 162) can control a movement along the curved axis 198. For example, a rotation of actuating element 154 about the Y-axis 158 (pivot axis 164) can control movement along the curved axis 200. In FIG. 6, resulting movements of the displayed image section 116 on the display unit 128 are indicated by curved double arrows 210, 212. It is understood that the display unit 128 usually comprises a flat screen. Therefore, the arrows 210, 212 are curved for illustration purposes only.

In other words, the mode of the handling device 10 shown in FIG. 6 allows the observation instrument 38 to orbit around the center of the image section 116, while the observation instrument 38 remains aligned with the center with its optical axis 104. Similar to a planet, the observation instrument 38 can orbit the center, while the optical axis 104 remains radially aligned with the center.

Again, it is noted that for instance for a stereo image capturing unit 118 (FIG. 3 and FIG. 4), the present alignment of the image capturing unit 118 (horizon 140) is determined and is taken into account in controlling by means of coordinate transformation, so that the operator can intuitively orientate himself on the displayed image section 116. Control pulses that are detected using the pivot axes 162, 164 lead to movements of the displayed image section 116 in the same direction along the resulting axes/paths 210, 212. Operation is significantly simplified.

It is basically conceivable to locate pivot point 194 also in the center of the displayed image section 116. This may be accompanied by the pivot point 194 eventually also coinciding with the center 124 of the sensor 120, 122 of the image capturing unit 118 (cf. FIG. 3). In this way, a double central alignment is provided.

As explained above in connection with FIG. 4, there may also be situations where the center of the displayed image section 116 does not coincide with the center 124 of sensor 120, 122. In such a case, it is still conceivable that the pivot point 194 in the center of the displayed image section 116 is selected. Accordingly, there is an offset between the pivot point 194 and the actual center 124 of the sensor 120, 122. This offset is taken into account by the control device 44, for instance by the handling control device 46, in the movement control of the observation instrument 38 along the curved path 198, 200. Nevertheless, the goal of the control is to keep the selected pivot point 194 in the center of the displayed image section 116.

However, it is also conceivable that a pivot point 214 is chosen, which is deliberately not in the center of the displayed image section 116. There is an offset between the center of the displayed image section 116 and the selected off-center pivot point 214. Thus, an off-center anchor point is mentally chosen as the center of the movement of the observation instrument on the curved surface 202. The control device 44, for instance the handling control device 46, can be adapted to maintain this offset, which is present on the display of the display unit 128, during movement. In other words, in this mode, the optical axis 104 of the observation instrument 38 is deliberately not aligned with the center of rotation, i.e. the off-center pivot point 214.

It is understood that the operating modes shown in FIG. 5 and FIG. 6 can be combined if the operator moves the actuating element 154 both translatorily (axes 156, 158) and rotationally (axes 162, 164). However, it is also conceivable to separate the two operating modes. Accordingly, there is a parallel shift mode, a pivot mode and a combined mode. The corresponding modes can be selected, for example, via the actuating elements 170 on the input device 50 or otherwise.

Figure 7:
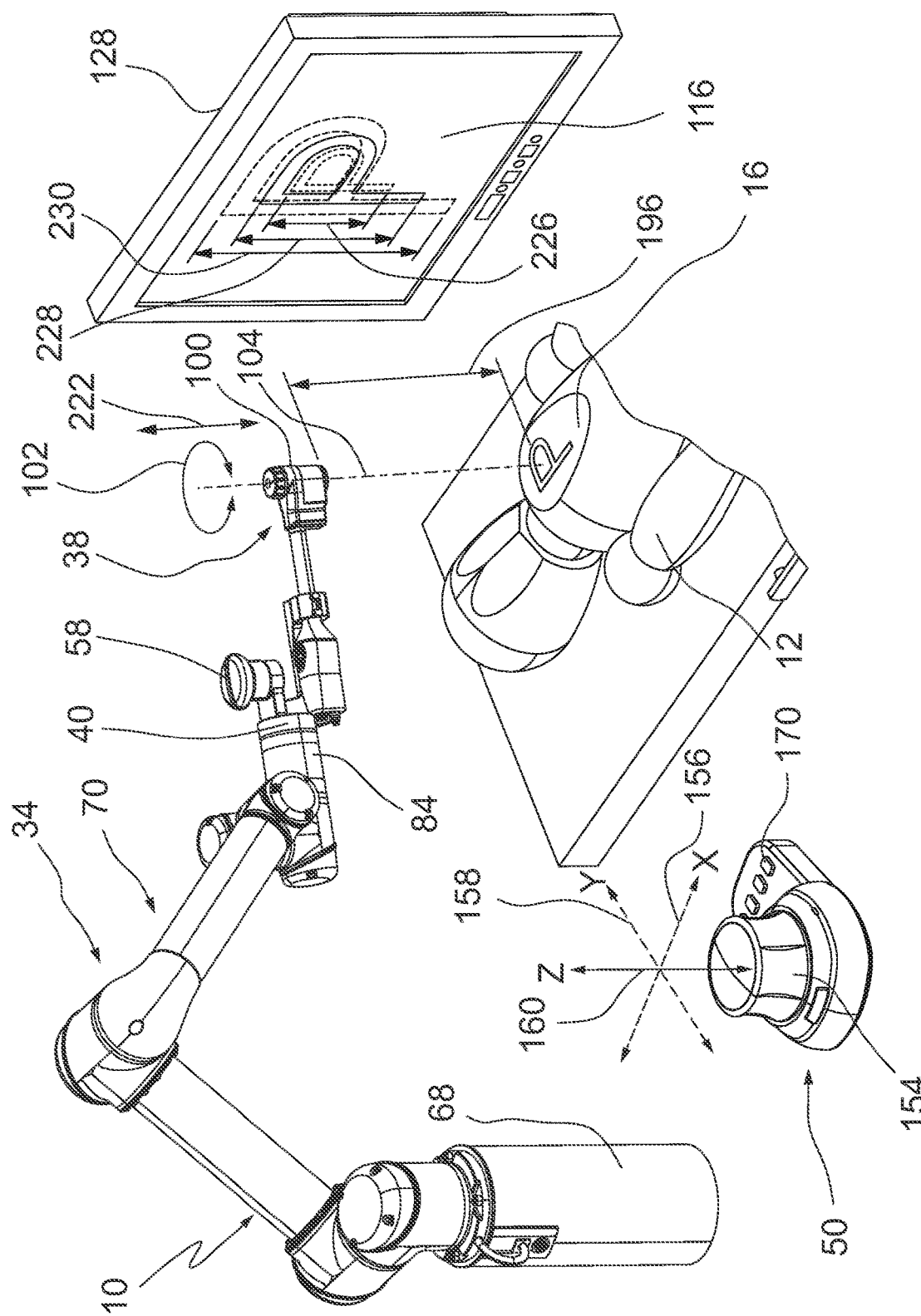
FIG. 7 is another partial perspective view of an embodiment of a handling device with an observation instrument to illustrate another exemplary function.

FIG. 7 illustrates the use of the input device 50 for controlling further functions of the optical observation instrument 38. By way of example, the lift axis 160 of the input device 50 can be used to induce a change in the object distance 196, cf. the interpolated axis 222. Using this function, an enlargement (detail increase) and/or increase in the magnification scale can be effected when the observation head 100 with the image capturing unit 118 moves closer to the object level/object field 16.

The result of a change of the working distance/object distance 196 is illustrated by the double arrows 226, 228, 230 in the displayed image section 116. When the working distance is decreased, the displayed image appears larger. When the working distance is increased, the displayed image appears smaller. In this way, a zoom function can be achieved—at least in terms of the result. This can be achieved by manipulating the actuating element 154. This can include pushing or pulling along the lift axis 160 (Z-axis). However, it is also conceivable to achieve this function by rotating the actuating element 154 about the Z-axis 160 (rotation axis 166).

At least in exemplary embodiments it is necessary to adjust the object distance of the optical unit of the observation head 100 so that the image appears sharp at the selected object distance. Here, again, one of the degrees of freedom of movement (cf. axes 160, 166) of the actuating element 154 of the input device 50 can be used to control a focus drive.

In alternative embodiments, an optical unit with variable focal length is integrated in the observation head 100, so that an optical zoom can be realized. In alternative embodiments, a so-called digital zoom is possible at least within limits. This is for instance the case when the reproduced image section 116 is smaller than the theoretically possible recording area 114 of the image capturing unit and/or smaller than the field of view of the optical unit. In this case, the captured and/or reproduced image section 116 can be varied at least slightly within the limits defined by the recording area 114, in order to enable an enlarged detail display or reduced overview display.

Furthermore, it is conceivable to couple the digital zoom with alternative measures for providing enlarged/reduced image sections in order to enable intuitive controlling of such an enlargement function via one and the same input device 50. The mode, in which the input device 50 is used to change the object distance 196 by moving the observation instrument 38 along the interpolated axis 222, can in principle be used simultaneously with the modes described in FIG. 5 and FIG. 6. However, it is also conceivable to separate the individual modes from each other in order to enable unambiguous operation.

Furthermore, in an exemplary embodiment it is conceivable to select a travel speed of the robotic handling unit and consequently of the observation instrument 38 mounted thereon dependent on a selected zoom level and/or as a function of a selected working distance/object distance 196. Accordingly, the observation instrument 38 can be moved more slowly if an enlarged display (high zoom factor, small object distance and/or large image scale) is selected. In this way, the changing image section 116 can still be captured well for the observer. Conversely, the observation instrument 38 can be moved faster if a reduced display (small zoom factor, large object distance and/or small image scale) is selected. This is possible because the displayed image section 116 covers a larger area of the object field 16.

Figure 8:
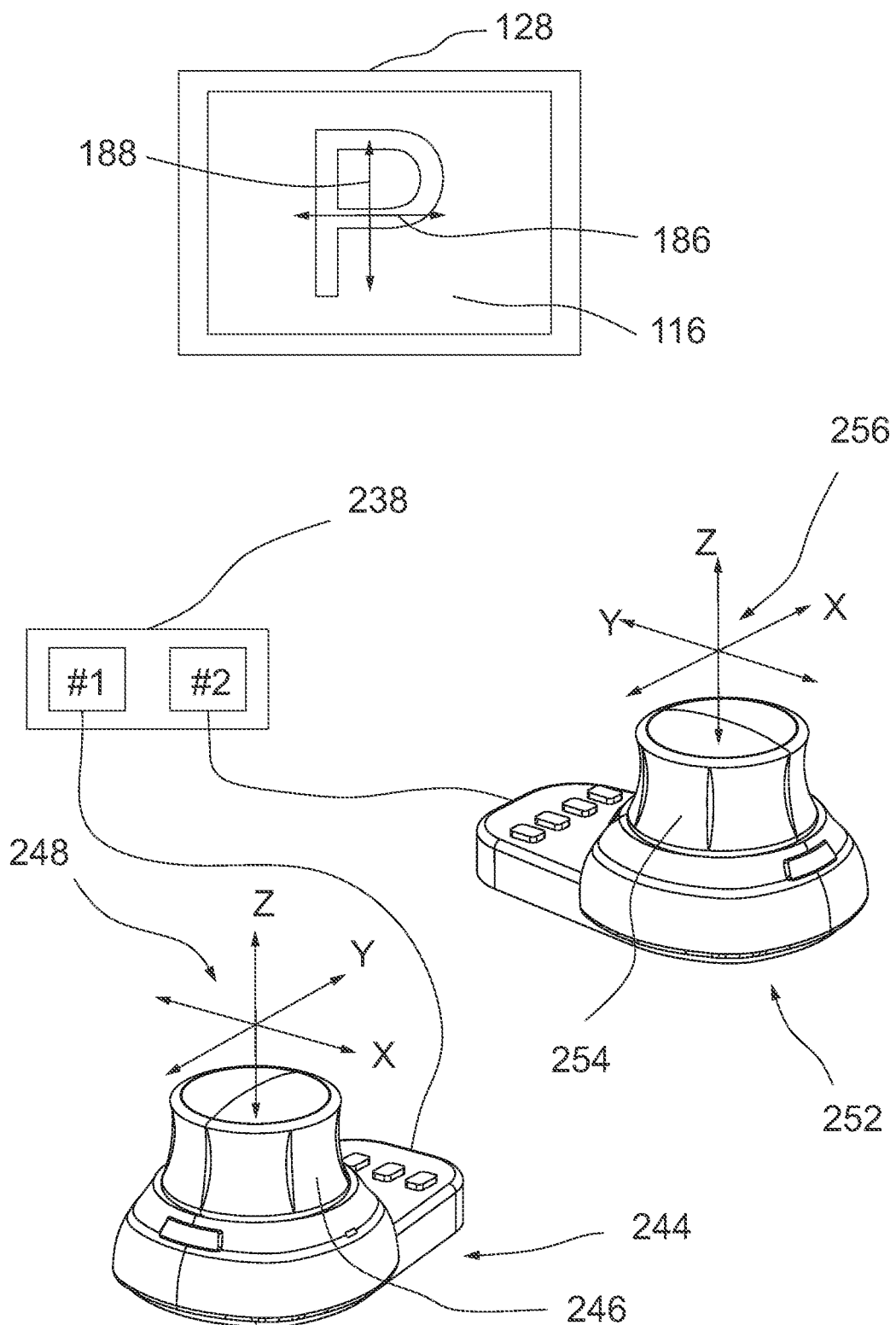
FIG. 8 is a schematic view of an arrangement comprising two input devices, which can be used for control purposes in the handling device.

FIG. 8 illustrates in conjunction with FIG. 1 that a plurality of input devices 244, 252 can be coupled via an interface 238 with the control device 44, i.e. the handling control unit 46 or the instrument control unit 48. In FIG. 8, the input devices 244, 252 are each single-handed input devices with an input element 246, 254, which can be operated in various room axes to generate control commands. Cf. the coordinate systems 248, 256 assigned to the input devices 246, 254. A plurality of input devices 244, 252 may be required to enable manipulations by different operators in the operating environment. On the one hand, this may involve controlling the robotic handling unit 34. It may also involve controlling the observation instrument 38, e.g. for controlling imaging parameters and/or image reproduction parameters.

It is understood that the control device 44 with the interface 238 uses a suitable activation/prioritization/hierarchy to define in a clear way, which of the input devices 244, 252 is currently used. In this way, for example, a primary input device 244 and a secondary input device 252 may be defined, wherein the primary input device 244 has a higher priority. Accordingly, the secondary input device 252 is deactivated and/or its commands are ignored if the primary input device 244 is used. Other measures for defining the currently used input device are conceivable.

The medical handling device 10 can basically be controlled via different types of input devices, cf. the input devices 50, 52, 54, 56 and 58 in FIG. 1. FIG. 8 shows two input devices 244, 252 of the same type. However, this is not to be understood as to be limiting.

Regardless of the current position and orientation of the input devices 244, 252, their users can orient themselves by the current image section 116 of the display unit 128 when controlling the robotic handling unit 34. In other words, the coordinate systems 248, 256 of the input devices 244, 252 are brought into alignment with the resulting movement axes 186, 188 of the displayed image section 116.

It is also conceivable to provide different display units 128, for example different monitors or HMDs for different users. This may include situations where users use different orientations (rotational orientation) of the displayed image section 116 on their assigned display unit. Then the respective input device 244, 252 and/or its coordinate system 248, 256 can be brought into alignment with the respective orientation of the image section in order to be able to move the image section intuitively. This can simplify the operation for different operators. For instance, in the medical domain it is conceivable that different persons are involved in a medical procedure. Accordingly, it is conceivable that the responsibility for operating the handling device 10 and/or the robotic handling unit 34 could be changed between those involved in the temporal sequence of a medical procedure.

Figure 9:
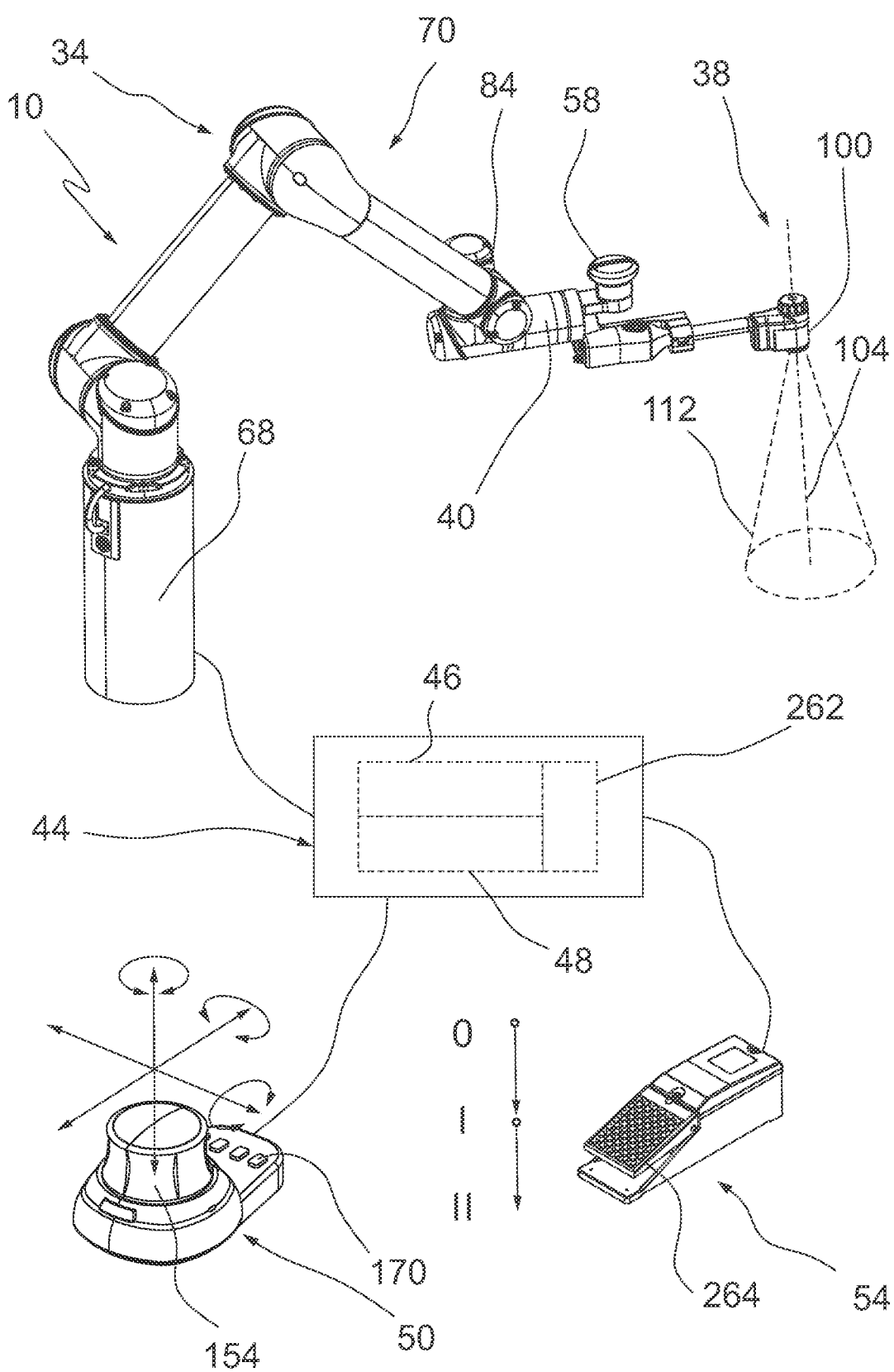
FIG. 9 is a perspective, simplified partial view of an embodiment of a handling device having an input element that acts as an enabling switch.

In conjunction with FIG. 1, FIG. 9 illustrates a release process for increasing safety when operating the handling device 10, for instance the robotic handling unit 34. For this purpose, a safety device 262 is provided, which may also be referred to as an enable control. The safety device 262 can be arranged as a component of the control device 44, cf. the schematic representation of the control device 44 with the handling control unit 46 and the instrument control unit 48 in FIG. 9.

The input device 50 can be used to control the robotic handling unit 34 so that links of the kinematic chain 70 are moved to move the observation instrument 38. This can have considerable consequences in case of errors or operating errors. Accordingly, in exemplary embodiments, an additional release process using an enabling switch is provided. An example of an enabling switch is the input device 54 and/or its input element 264. The input element 264 is arranged as a foot switch, for example. The enabling switch has a double function, since it enables the movement of the robotic handling unit 34, and it can also be used to switch back and forth between the control of the observation unit 38 and the robotic handling unit 34.

It is to be noted that the input device 56 (cf. FIG. 1), which is arranged on the platform 22, can also be used as an enabling switch. Accordingly, the safety device 262 can be configured in such a way that controlling the handling unit 34 is only possible if a corresponding mode is activated via the input device 54.

The safety device 262 ensures that only deliberate manipulation of the current position of the observation instrument 38 is possible. Operating errors/unconscious operations can be avoided.

In exemplary embodiments, the input device 54 is hard-wired to the safety device 262. In other words, the safety device 262 can be a discrete safety device, which is not only implemented by software in the control device 44. In this way, the safety device 262 is designed independently. This makes manipulations more difficult. A fixed coupling of the input device 54 (hard-wired) makes manipulation of the input device 54 more difficult.

The input device 54 and/or its input element 264 has/have at least two switch positions. A first switching position (stage 0) corresponds to an unactuated state, for example. In this state, the input device 50 cannot be used to control and move the handling unit 34. A second switch position (stage I) can cause a state, in which the input device 50 is activated, so that commands at the input device 50 are processed by the control device 44 to control and move the handling unit 34.

To further increase safety, at least in exemplary embodiments a third stage (stage II) is provided, which can also be referred to as panic mode/panic stage. The second stage (stage I) is provided for this embodiment between the first stage (stage 0) and the third stage (stage II). In other words, the operator must apply a certain minimum force to move the input element 264 of the enabling switch from the first stage (deactivation state) to the second stage (activation state). However, this actuating force must not exceed a defined maximum force. If the maximum force is exceeded, input element 264 of the enabling switch is moved from the second stage (activation state) to the third stage (deactivation state or panic state). A defined actuating force must therefore be applied, which lies in a range between a minimum force and a maximum force, in order to be able to control the robotic handling unit 34 via the input device 50.

This arrangement further increases safety. Namely, if the enabling switch in the form of the input device 54 is unintentionally actuated with high force, the input device 50 is not necessarily enabled for operating commands. Instead, the activation state/enabled state (second stage and/or stage I) is passed through and/or skipped and the input device 54 is set to the third stage (stage II).

It is understood that the enabling switch may also be configured differently. For example, it is conceivable to deliberately operate the enabling switch with only a first stage (stage 0) and a second stage (stage I). Other actuating elements may be provided, such as additional operating elements, which must be actuated together with the enabling switch. In the embodiment shown in FIG. 9 the enabling switch is arranged as input device 54 in the form of a foot switch. It is understood that also manually operated switches can be used as enabling switches.

Figure 10:
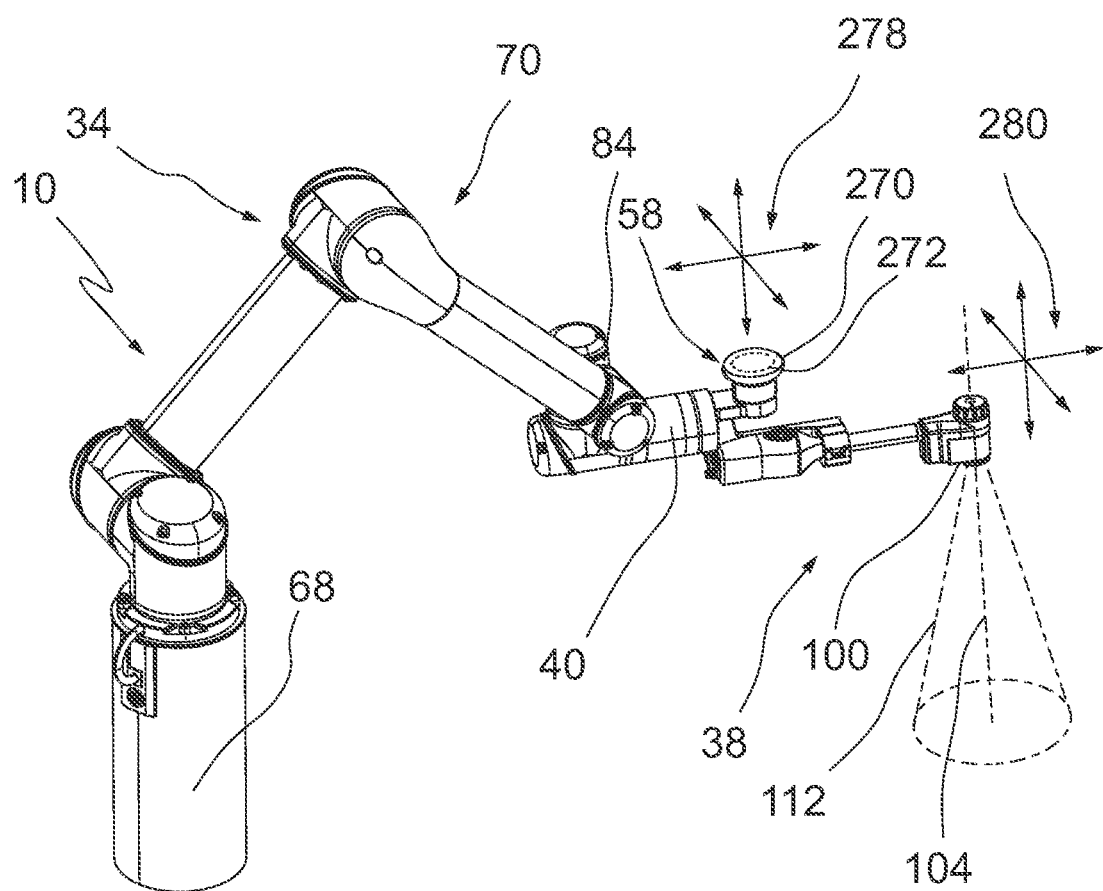
FIG. 10 is an additional perspective partial view of an embodiment of a handling device with an observation instrument to illustrate another exemplary function.
Figure 10:
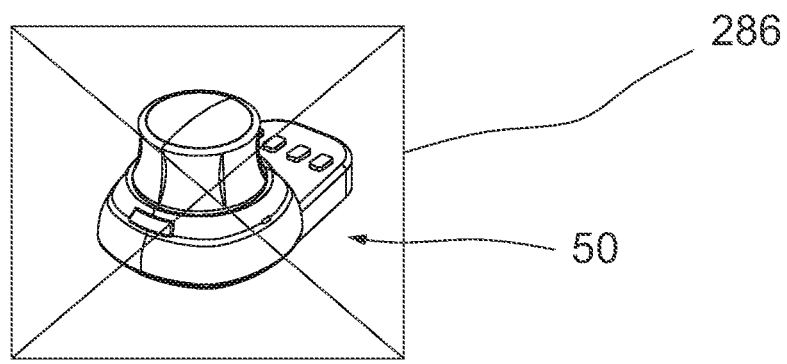

FIG. 10 illustrates another exemplary operating mode of the handling device 10, for instance the handling unit 34. The operating mode illustrated in FIG. 10 can also be referred to as direct control mode. In the direct control mode, the robotic handling unit 34 is not controlled via the input device 50, cf. the crossed-out block marked 286 in FIG. 10.

Instead, in the direct control mode, the control of the handling unit 34 is carried out directly by a manipulation and/or an engagement on an element of the kinematic chain 70 of the handling unit 34. For this purpose, in the embodiment shown in FIG. 10 there is provided the input device 58, which comprises an input element 270 in the form of a handle or knob. The operator can grasp the input device 270 and move it in space. The input device 58 with the input element 270 is exemplarily arranged on the instrument holder 40 of the robotic handling unit 34, i.e. in the immediate vicinity of the supported observation instrument 38. The input device 58 can also be referred to as a direct control input device.

At least in an exemplary embodiment, the input device 58 at the input element 270 comprises a sensor 272, which detects, for example, an approach or presence of the operator's hand. In this way, the control of the handling unit 34 can be enabled via the input device 58 in the direct control mode.

It is conceivable to dispense with an additional release for the release of the direct control mode using a sensor 272 in input element 270 of the input device 58 (cf. the input device 54 that is used as enabling switch in FIG. 1 and FIG. 9). This is conceivable because the operator can directly, or almost directly, influence the position and orientation of the observation instrument 38 mounted on the instrument holder 40 via the input device 58. In such a case, the operation is clearly and directly possible.

In the direct control mode, force and travel impulses applied by the operator to the input element 270 of the input device 58 are detected and evaluated by the handling control unit 46 (cf. FIG. 1), wherein drives of the elements of the robotic handling unit 34 are controlled in such a way that the robotic handling unit 34 with the instrument holder 40 and the observation instrument 38 mounted thereon follows the induced movement at the input device 58. It is to be noted that in the direct control mode both translational movements and rotary movements/pivot motions of the observation instrument 38 mounted on the handling unit 34 can be effected.

The acquisition of the operating impulses can be done by monitoring the various axle drives of the kinematic chain 70 of the handling unit 34. The operating impulses can be sensed in the axle drives and can therefore be detected. Alternatively, corresponding sensors can be assigned to the axle drives.

Alternatively or additionally, it is conceivable to provide the input device 58, similar to the input device 50, with its own degrees of freedom of movement and corresponding sensors to detect deflections. It is also conceivable to provide force/deformation sensors for the input device 58 and/or its input element 270 to record how the operator wants to move the handling unit 34 with the observation instrument 38.

In the direct control mode, the control device 44, for instance the handling control unit 46, controls the handling unit 34 in such a way that it follows the movement impulses of the operator at the direct control input device 58, and that the current position and/or orientation is maintained when the operator no longer acts on the input device 58. In this way, the operator can move the observation instrument 38 quasi-manually, involving direct and immediate feedback.

In FIG. 10, an input coordinate system 278 is assigned to the input element 270 of the input device 58. A coordinate system 280 that is aligned therewith illustrates the resulting interpolated movement for moving the observation instrument 38 via operating impulses at the input device 58. The observation instrument 38 follows the operating impulses at the input device 58 directly due to the proximity between the input device and the observation instrument 38.

The handling control unit 46 can be operated in such a way that the operator feels a certain, but not too great resistance (braking torque) in the direct control mode when operating the input device 58. This allows sensitive movement and position setting in the direct control mode.

It is also conceivable to use the control device 44 in the direct control mode, for instance its handling control unit 46, to record the movement path of the handling device 34 manually controlled by the operator via the input device 58 and to run it "backwards" if necessary. In this way, the control device 44, for instance its handling control unit 46, can provide a return function. The device can therefore move to the start position or another position that has been stored, starting from the current position. This is also possible in other control modes, not only in the direct control mode. For example, the storage and recall of selected functions can be controlled via the actuating elements 170 on the input device 50 or via other actuating elements.

Figure 11:
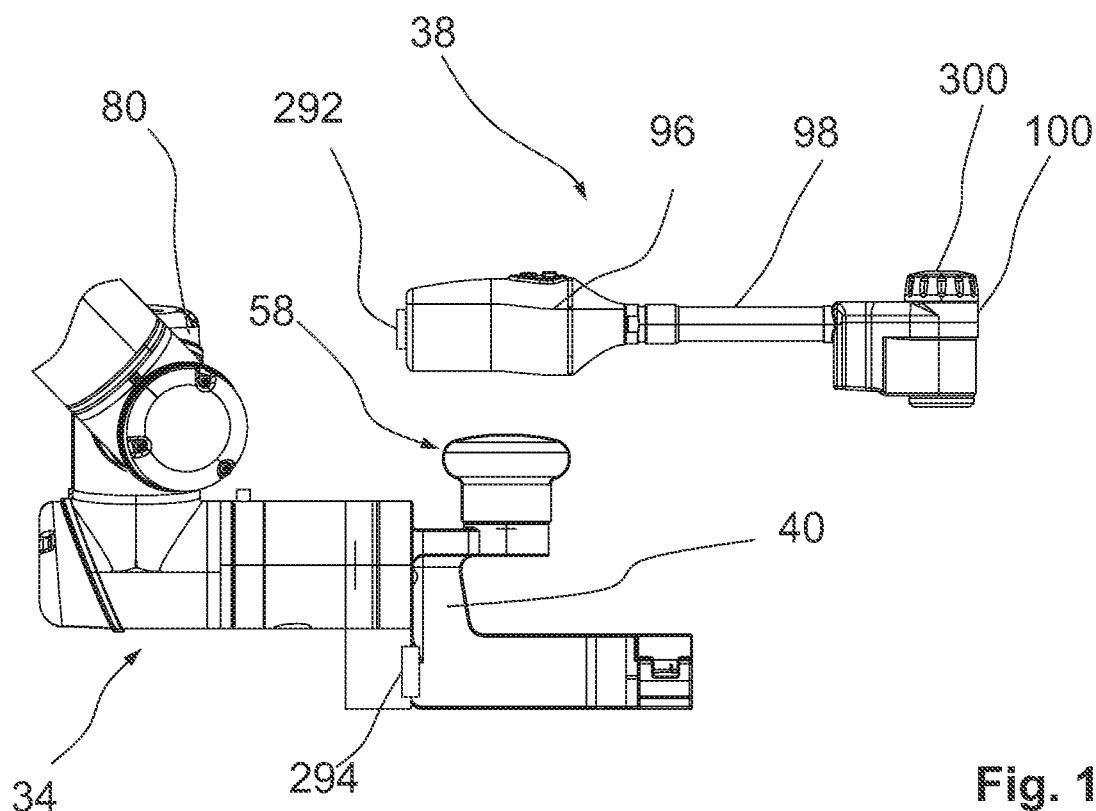
FIG. 11 is a side view of an instrument holder with an observational instrument that can be mounted thereon, in an unmounted state.
Figure 12:
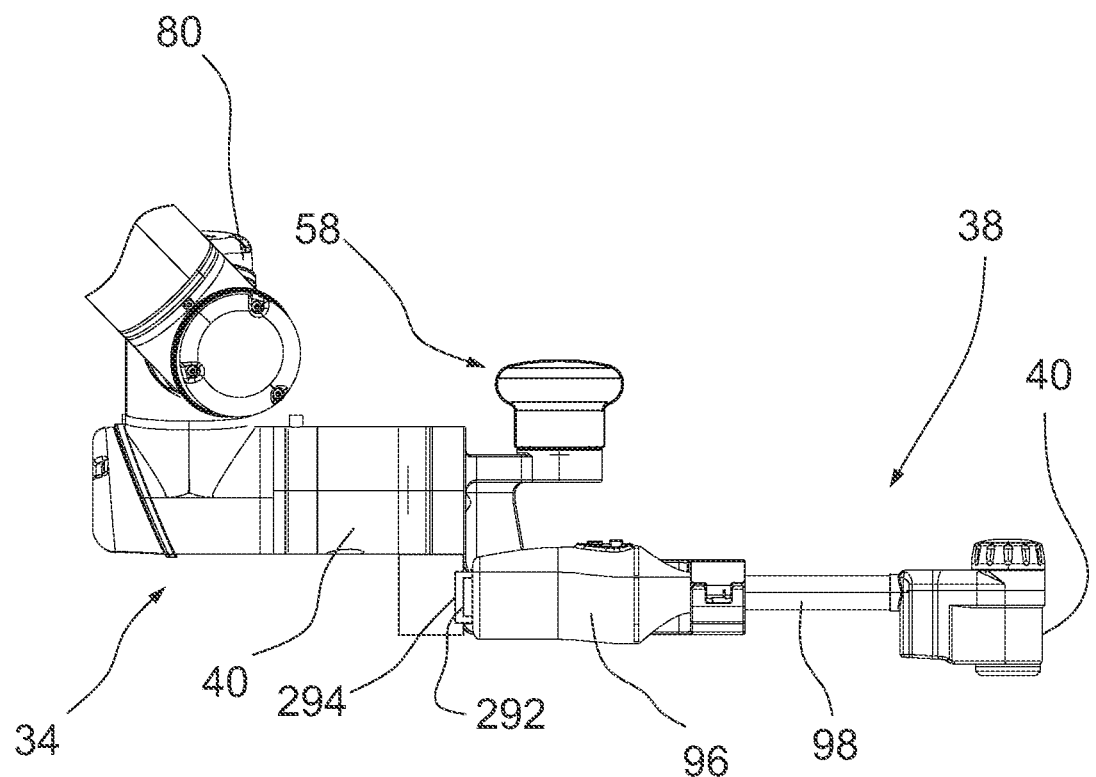
FIG. 12 is another view of the arrangement according to FIG. 12 in a mounted state.

FIGS. 11 and 12 illustrate the attachment of the observation instrument 38 to the instrument holder 40 of the handling unit 34. In FIG. 11, the observation instrument 38 is detached from the instrument holder 40. In FIG. 12, the observation instrument 38 is attached to the instrument holder 40. In addition to the mechanical coupling between the observation instrument 38 and the instrument holder 40, a coupling—in terms of signaling—via interfaces 292, 294 is also provided. An interface of the observation instrument is designated by 292. An interface on the part of the handling unit 34 is designated by 294. Accordingly, together with the mechanical coupling, a coupling in terms of signaling may also take place.

In connection with the attachment of the observation instrument 38, the control device 44 of the handling device 10 can therefore determine via the interfaces 292, 294, which type of instrument the observation instrument 38 is. Such an identification can be used for an instrument type-specific basic setting (parameter set) of the handling unit 34. By way of example, this can involve taking into account the present dimensions of the observation instrument when controlling the robotic handling unit 34. Furthermore, it is conceivable to exchange information relating to a rotary drive 300 for the image capturing unit (not explicitly shown in FIGS. 11 and 12) on observation head 100 via interfaces 292, 294. Furthermore, it is conceivable to obtain information relating to a current orientation/rotational position of the image capturing unit.

Via the interfaces 292, 294, image information can be transmitted, e.g. image signals of the monitored image section and/or recording area. In addition, information is transmitted, which can be used for the operation of the robotic handling unit 34.

It is conceivable that the observation instrument 38 contains identification information (ID), which can be requested via interface 292, 294. Accordingly, the control device 44 could then request a parameter set relating to the observation instrument 38 on the basis of this information, e.g. in a database. It is also conceivable that the observation instrument 38 itself could provide this information via interface 292, 294.

The arrangement illustrated in FIGS. 11 and 12 relates to the exchange of information between the observation instrument 38 and, on the one hand, the handling control unit 46 and, on the other hand, the instrument control unit 48. Respective signals/information are transmitted via the interposed handling unit 34.

Figure 13:
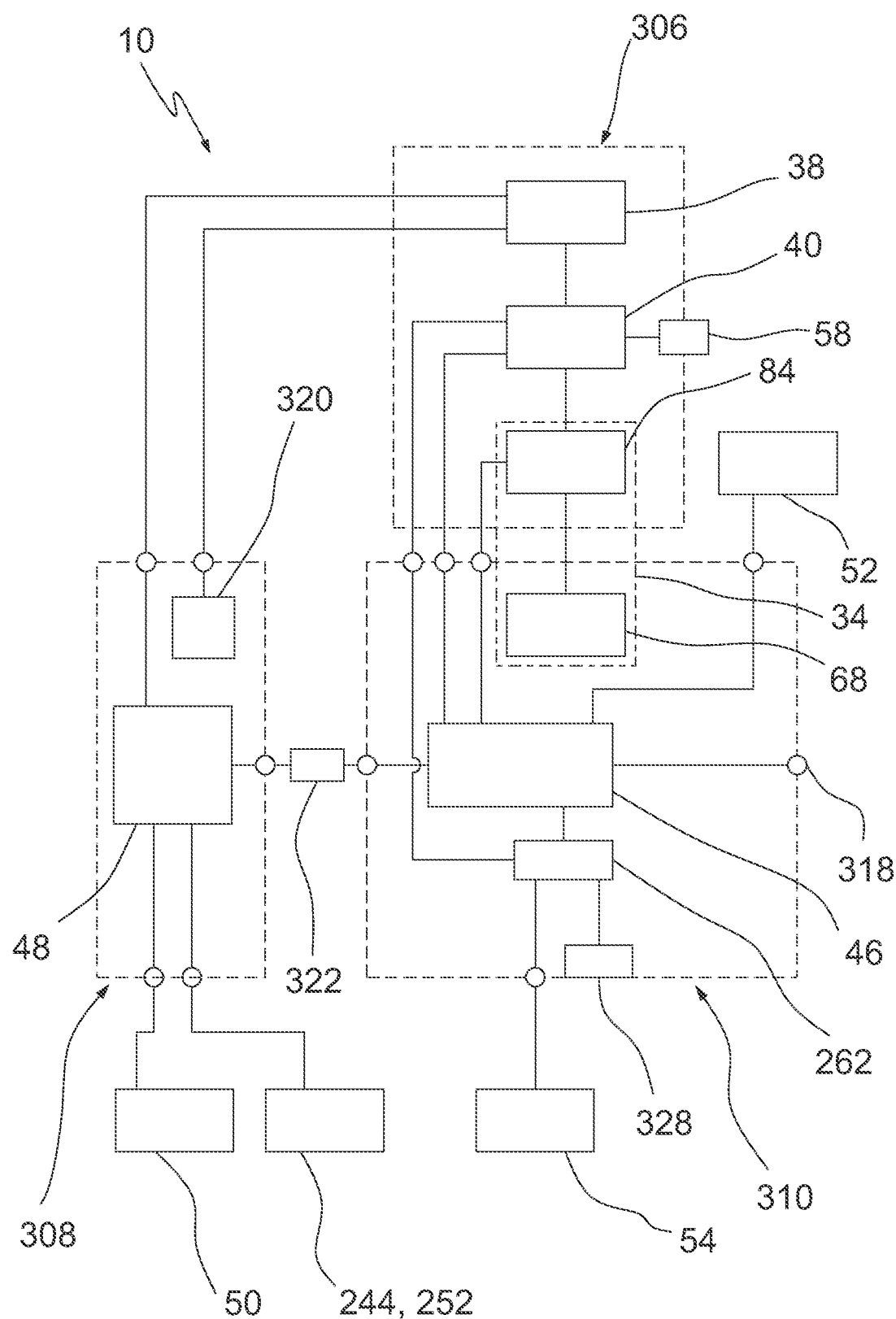
FIG. 13 is a schematic block diagram to illustrate a principle design of an embodiment of a handling device.

FIG. 13 illustrates with reference to a schematic representation a block diagram to illustrate an exemplary functional arrangement/system architecture of a handling device 10. From a structural point of view, the handling device 10 shown in FIG. 10 can basically correspond to the design of the handling device 10 illustrated in FIGS. 1 to 12.

The handling device 10 comprises an observation section 306, an instrument control section 308 and a handling section 310. The sections 306, 308, 310 are functionally separate sections. They are not necessarily structurally separate sections. The observation section 306 comprises the observation instrument 38 mounted on the holder 40. Furthermore, input device 58 for the direct control mode is assigned to observation section 306. By way of example, the input device 58 comprises a sensor for activating the direct control mode.

A mechanical connection between observation section 306 and handling section 310 is provided via the robotic handling unit 34, which is equipped with the hand 84, for example, which supports the instrument holder 40, cf. FIG. 2. The handling unit 34 also comprises a base and/or frame 68, which is assigned to handling section 310. The handling section 310 also includes the handling control unit 46 for controlling the handling unit 34. The handling unit 46 is provided with an interface 318 for power supply. The interface 318 can also be used for information exchange and/or media supply.

In addition, the handling section 310 is also assigned—in terms of structure—with the input device 52, which is arranged as a touch monitor, by way of example. The input device 52 is coupled with the handling control unit 46 and therefore also with the (global) control device 44. The handling section 310 also includes the safety device 262, which can also be referred to as an enable control. By way of example, the safety device 262 is coupled with the input device 54, which is arranged as an enabling switch. By way of example, in terms of signaling for example, coupled to the handling control unit 46 in order to enable or block operating modes of the handling control unit 46 and, consequently, of the handling unit 34.

In the exemplary embodiment shown in FIG. 13, safety device 262 is also coupled with a locking sensor 328, which monitors whether platform 22 supporting the handling unit 34 and/or cart 24 is braked and secured. At least in exemplary embodiments, this is also a condition for releasing the movement of the handling unit 34.

The instrument control section 308 basically involves the instrument control unit 48, i.e. the CCU/console for monitoring and controlling the observation instrument 38. Accordingly, the instrument control unit 48 is coupled to the observation instrument 38 via at least one signal line. In addition, the embodiment in FIG. 13 is provided with a light source 320, which is coupled to the observation instrument 38 for illuminating purposes.

FIG. 13 also illustrates lines for signal and/or information exchange between observation section 306, instrument control section 308 and handling section 310

Furthermore, at least one input device 50, 244, 252 is coupled to the instrument control unit 48 via a suitable interface. It is possible to provide a plurality of input devices 50, 244, 252, so that different operators can control the handling device 10. The instrument control unit 48 and the at least one input device 50, 244, 252 are configured in such a way that they can also be used for control in a hand-guided mode of the observation instrument 38. In other words, the instrument control unit 48 coordinates the imaging and, if necessary, the image reproduction. The at least one input device 50, 244, 252 can also be used for controlling imaging parameters and image reproduction parameters.

However, according to the embodiment illustrated in FIG. 13, it is provided that the at least one input device 50, 244, 252 coupled with the instrument control unit 48 is also to be used for controlling the robotic handling unit 34. For this purpose, the instrument control unit 48 is connected to the handling control unit 46, for example via an interface 322 for information exchange. The interface 322 can also be referred to as a network interface or data bus interface.

This configuration has the effect that in a mode, in which the input device(s) 50, 244, 252 can be used to control the robotic handling unit 34 for moving the observation instrument 38 mounted thereon, the instrument control unit 48 does not itself process the corresponding control signals extensively, but instead forwards and/or passes them on to the handling control unit 46 via the interface 322. Such a mode is enabled, for example, via the input device that is arranged as enabling switch 54, using the safety device 262.

A potential advantage of this design is that the instrument control unit 48 can still be used independently and autonomously for controlling the observation instrument 38, for example in a hand-held/hand-guided mode. This also applies to any input devices 50, which are directly coupled with the instrument control unit 48. This is also possible without the handling unit 34 and its handling control unit 46.

Nevertheless, the extended scope of use can be controlled by providing the robotic handling unit 34 using one and the same input device 50. It is therefore not strictly necessary to provide an additional input device 50 for controlling the handling unit 34. Instead, the input device 50 can be used in different modes for instrument control and handling control.

This is for instance conceivable if the input device 50 is a multi-axis input device. Such input devices (cf. a so-called 3D mouse) are well suited for both control modes. The potential advantage is that one and the same arrangement can be used for a hand-held operation of the observation instrument 38 and an operation assisted by the robotic handling unit 34. It is not strictly necessary to invest twice in the observation instrument 38 and its associated instrument control unit 48. Nevertheless, simple and safe operation of the extended arrangement of the handling device 10 with the robotic handling unit 34 is ensured.

A further aspect of the present disclosure relates to the use of present operating parameters and/or general parameters of the observation instrument 38 by the control device 44, for instance by its handling control unit 46, for controlling the robotic handling unit 34. For instance, exemplary embodiments are conceivable, in which the travel speed of the robotic handling unit 34 is made dependent on operating parameters of the observation instrument 38. This can, relate to a present object distance for example. If the object distance is large, a high travel speed can be selected for moving the observation instrument 38, and if the object distance is small, a low travel speed can be selected.

Figure 14:
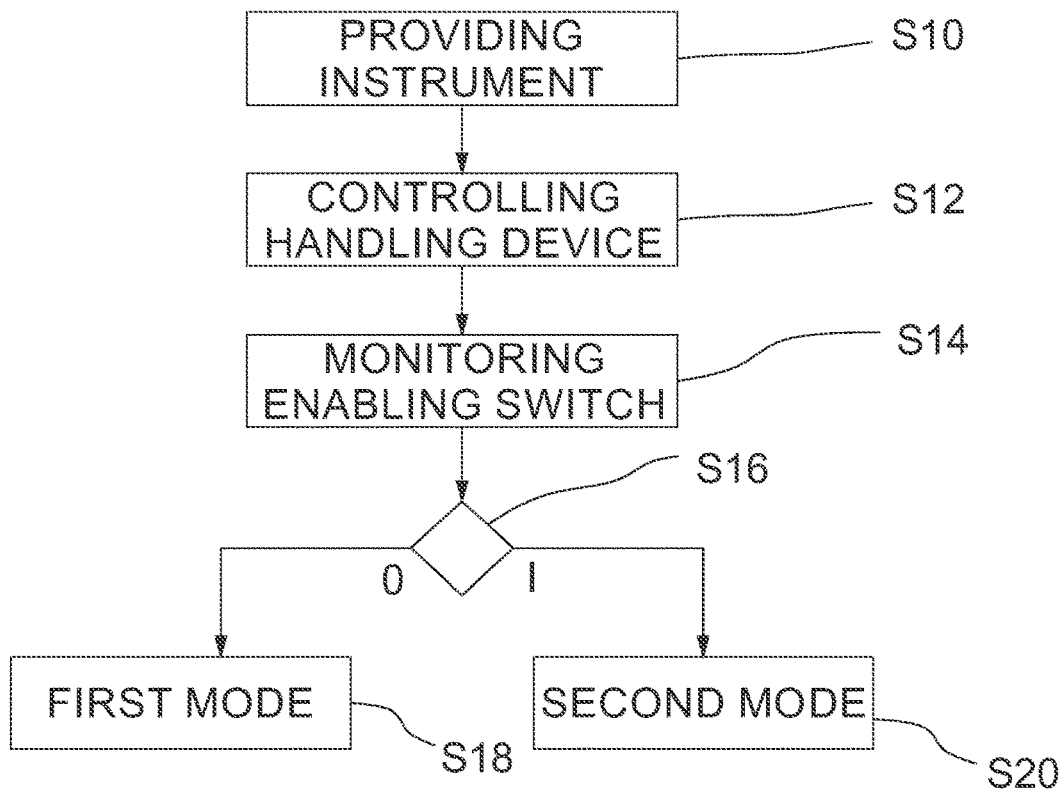
FIG. 14 a schematic, simplified block diagram to illustrate an embodiment of a method for controlling a handling device for an instrument.

With reference to FIG. 14, with the aid of a schematic block diagram, an exemplary embodiment of a method for controlling a handling device is elucidated. The handling device can be a medical handling device. However, it can also be a non-medical handling device.

The method comprises a step S10, which comprises the provision of an instrument and mounting it on an instrument holder on a robotic handling unit. The instrument is exemplarily an observation instrument. This is followed by a step S12, which comprises the control of the handling device with an input device, wherein the control relates to the control of the robotic handling unit and/or the instrument. In other words, there are different operating modes for the control device and/or the input device. For example, the control device comprises an instrument control unit for controlling the instrument and a handling control unit for controlling the robotic handling unit. The input device can be used both for controlling the robotic handling unit and for controlling the instrument.

In a further step S14, an enabling switch is monitored. The enabling switch is a foot switch, for example. Other designs are conceivable. The enabling switch can have different positions/states.

In a step S16, it is determined whether the enabling switch is in a first state 0 or a second state I. The first state 0 corresponds to a non-activated state. The second state I corresponds to an activated state. By way of example, the operator can apply a certain actuating force to change the enabling switch from the first state 0 to the second state I.

If the enabling switch is in the first state 0, a step S18 follows. Accordingly, the input device is in a first operating mode. In the first operating mode, the instrument can be controlled. In the first mode, however, there is no controlling of the robotic handling unit to move the instrument. As a result, relative movements between the instrument and a target object, such as an observation object, are reduced or avoided in the first operating mode.

However, if it is determined in the step S16 that the enabling switch is in the second state I, a step S20 follows. In the step S20, the input device can be operated in a second operating mode. In the second operating mode, the input device can therefore be used to control the robotic handling unit to move the instrument. However, this is only possible after explicit release by pressing the enabling switch. In this way, the second operating mode can only be activated by an additional release of this mode. This reduces the likelihood of unconscious activation of the second operating mode.

Figure 15:
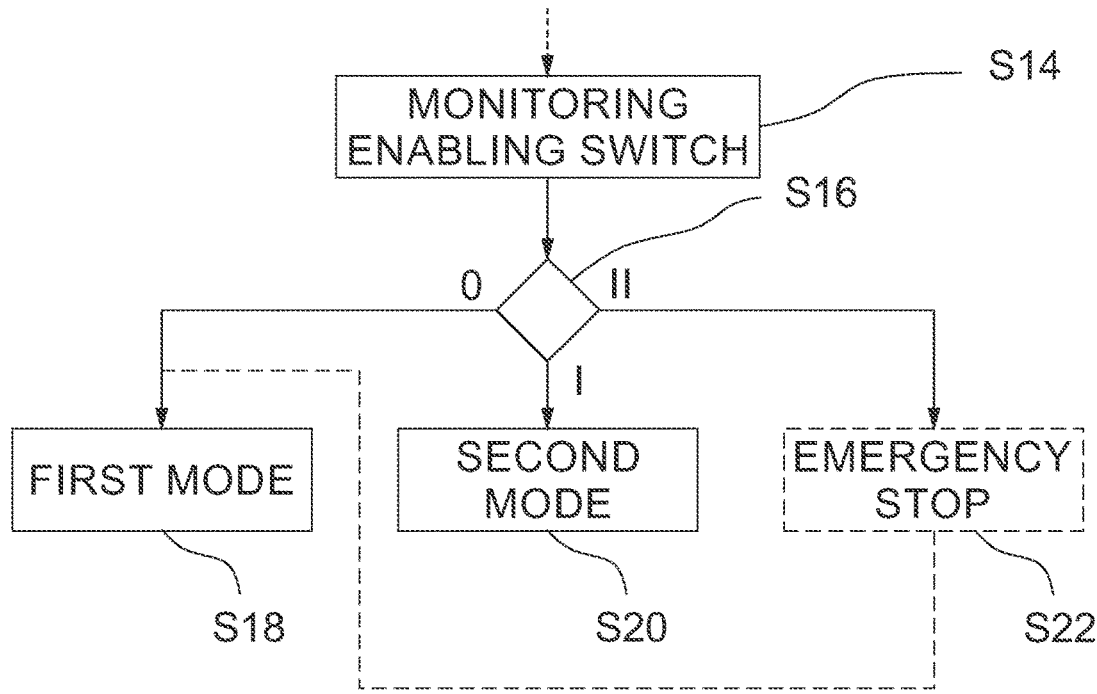
FIG. 15 is another schematic, simplified block diagram to illustrate another embodiment of a method for controlling a handling device for an instrument.

FIG. 15 illustrates a further exemplary embodiment of a method for controlling a handling device using a schematic block diagram. The method illustrated in FIG. 15 is based on the design shown in FIG. 14. With regard to the steps S10 to S14, it is therefore referred to the above explanations in connection with FIG. 14.

The embodiment shown in FIG. 15 uses an enabling switch that has three states/positions 0, I and II. Accordingly, the step S16 determines whether the enabling switch is in the first state 0, the second state I or the third state II. The first state 0 corresponds to a non-activated state. The second state I corresponds to an activated state. The third state II is reached when the actuating force of the operator on the enabling switch increases above a defined limit. In this way, the likelihood of operating errors can be further reduced. That is, if the enabling switch is unintentionally actuated with high force, the enabling switch changes from the first state 0 via the second state I to the third state II. In other words, the operator has to keep the actuating force within a certain range to bring about and maintain the second state I of the enabling switch. In other words, the enabling switch is designed with three stages, the second stage (activation of the second operating mode) being between the first stage and the third stage.

If it is determined in the step S16 that the enabling switch is in the first state 0, a step S18 follows. In the step S18, the input device is in the first operating mode. If it is determined the in step S16 that the enabling switch is in the second state I, a step S20 follows. In the step S20, the input device is in the second operating mode.

If it is determined in the step S16 that the enabling switch is in the third state II, a step S22 follows. The step S22 can basically be arranged as an emergency stop function. Accordingly, at least partial functions of the handling device are deactivated when the enabling switch is in the third state. Alternatively, it is conceivable that the third state II of the enabling switch is handled similarly to the first state 0. Accordingly, the input device is in the first operating mode (cf. the optional dotted line between steps S22 and S18).

The use of the enabling switch increases the operating safety. The risk of operating errors can be reduced. Relative movements of the instrument in relation to the target object/patient can be controlled after release with the input device that is intended for controlling the instrument's own functions.

What is claimed is:

1. A medical handling device, comprising:
    an instrument holder configured to hold one imaging instrument at a time,
    a robotic handling unit configured to support the instrument holder,
    a control device that comprises a handling control unit configured to control the robotic handling unit and an instrument control unit configured to control the instrument, wherein the control device comprises an interface for at least one input device,
    an input device that is coupled to the interface, wherein the input device is operable in a first operating mode to control the instrument, and in a second operating mode to control the robotic handling unit, wherein in the first operating mode the robotic handling unit is blocked from controlling movement of the instrument relative to a patient, and
    an enabling switch that is configured as a foot switch to which an operator applies force to switch between operating modes, the enabling switch adapted to activate the second operating mode upon a greater force being applied to the enabling switch than the force required for the first operating mode, wherein in the second operating mode the robotic handling unit is movable in response to input commands at the input device, wherein the enabling switch provides switching between at least two states, wherein a first state is an initial state, and a second state, where the greater force is applied, is an activation state for the second operating mode, wherein the enabling switch switches between states starting from the first state by applying the greater force which causes the enabling switch to switch to the second state and then with an increased actuating force into a third state, and wherein the control of the robotic handling unit is blocked both in the first state and in the third state of the enabling switch.

2. The handling device of claim 1,
    wherein the input device is arranged to be coupled to the control device via the interface,
    wherein the control device is arranged to be coupled to the instrument and to the robotic handling unit, and
    wherein the control device is interposed, in terms of signals, between the input device and the instrument that is supported by the instrument holder.

3. The handling device of claim 2, wherein the control device is interposed, in teens of signals, between the input device and the robotic handling unit.

4. The handling device of claim 1,
    wherein the enabling switch is directly connected to a handling control unit that is associated with the robotic handling unit.

5. The handling device of claim 1,
    wherein the control device is adapted to provide in the second operating mode control commands for the robotic handling unit, which have been detected via the input device, to the handling control unit via the instrument control unit.

6. The handling device of claim 5,
    wherein in the second operating mode, the control commands for the robotic handling unit are transmitted via the instrument control unit, which forwards the control commands.

7. The handling device of claim 1,
    wherein the input device is arranged as a multi-axis input device that detects operating movements in the form of travel motions or pivot motions in at least two axes, and
    wherein the operating movements are converted into control commands for the robotic handling unit.

8. The handling device of claim 7,
    wherein the robotic handling unit comprises a multi-link kinematics having a plurality of coupling links, and
    wherein the control device is adapted to convert the movement instructions by interpolation into control commands for movement axes of the coupling links.

9. The handling device of claim 8,
    wherein an operating element is provided for controlling the robotic handling unit in the direct control mode, and
    wherein the operating element comprises a sensor for generating an enabling signal for the direct control mode.

10. The handling device of claim 1,
    wherein the control device is adapted to store a current position and orientation of the instrument and to recall it on request.

11. The handling device of claim 10,
    wherein the control device is adapted to store a plurality of predefined positions and orientations of the instrument in order to recall them on request.

12. The handling device of claim 1,
    wherein the control device is adapted to control the robotic handling unit in such a way that the instrument is pivotable about a virtual pivot axis, which is arranged parallel to an image capturing unit, by interpolated movement of the robotic handling unit.

13. The handling device of claim 1,
    wherein the control device is adapted to operate the robotic handling unit in a direct control mode in order to move and align the instrument in space,
    wherein operating commands are generated at the robotic handling unit by acting on an element of the robotic handling unit, which is adjacent to the instrument, and
    wherein the handling control unit is adapted to control the robotic handling unit in such a way that the instrument follows an induced movement.

14. The handling device of claim 1,
wherein the robotic handling unit is mounted on a cart, and
wherein the control of the robotic handling unit for moving the instrument is only enabled when the cart is blocked.

15. The handling device of claim 1,
wherein the interface is arranged to be coupled to a plurality of input devices, via which the robotic handling unit is controllable, and
wherein the input devices can be prioritized differently.

16. A medical handling device, comprising:
an instrument holder configured to hold a single observation instrument,
a robotic handling unit configured to support the instrument holder,
a control device comprising a handling control unit configured to control the robotic handling unit and an instrument control unit configured to control the instrument, wherein the control device comprises an interface for at least one input device,
an input device coupled to the interface, wherein the input device is operable in a first operating mode for controlling the instrument and in a second operating mode for controlling the robotic handling unit, and
an enabling switch configured as a foot switch that activates the second operating mode, in which the robotic handling unit is movable in response to input commands at the input device,
wherein in the first operating mode the robotic handling unit is blocked from controlling movement of the instrument relative to a patient,
wherein the input device is coupled to the control device via the interface,
wherein the control device is coupled to the instrument and to the robotic handling unit,
wherein the control device is interposed, in terms of signals, between the input device and the instrument that is supported by the instrument holder, and
wherein the control device is adapted to provide, in the second operating mode, control commands for the robotic handling unit based on an increased force applied to the enabling switch that switches the enabling switch from the first operating mode to the second operating mode, the control commands having been detected via the input device, and provided to the handling control unit via the instrument control unit.

17. A method to control a handling device comprising a robotic handling unit having an instrument holder and a single instrument mounted thereon, the method comprising:
providing the instrument at the instrument holder,
controlling one or more of the instrument and the robotic handling unit via a control device,
wherein the controlling is performed using an input device,
wherein the input device is operable in a first operating mode for controlling only, the instrument and in a second operating mode for controlling the robotic handling unit, wherein in the first operating mode the robotic handling unit is blocked from controlling movement of the instrument relative to a patient, and
activating the second operating mode, in which the robotic handling unit is movable in response to input commands at the input device, by actuating an enabling switch through an increase in pressure applied thereto to switch the enabling switch from the first operating mode to the second operating mode, wherein the enabling switch is operable in a first state, a second state and a third state depending on the increase in pressure, wherein the second state is an activation state for the second operating mode, wherein the second operating mode that controls movement of the instrument relative to a patient is deactivated in the first state and in the third state, and wherein the second state is positioned between the first state and the third state on the enabling switch, and the enabling switch is configured as a foot switch.

18. A method to operate a medical handling device comprising:
providing an instrument holder that holds a single observation instrument, and a robotic handling unit that supports the instrument holder,
controlling the robotic handling unit and an instrument control unit that controls the instrument via a controller, wherein the controlling is performed using an input device that is coupled to the interface,
wherein the input device is operable in a first operating mode to control the instrument and in a second operating mode to control the robotic handling unit, and
activating, via an enabling switch configured as a foot switch, the second operating mode by increasing a pressure on the enabling switch, wherein in the second operating mode the robotic handling unit is movable in response to input commands at the input device,
wherein in the first operating mode the robotic handling unit is blocked from controlling movement of the instrument relative to a patient,
wherein the input device is coupled to the control device via the interface,
wherein the control device is coupled to the instrument and to the robotic handling unit,
wherein the control device is interposed, in terms of signals, between the input device and the instrument that is supported by the instrument holder, and
wherein the control device is adapted to provide in the second operating mode control commands for the robotic handling unit, which have been detected via the input device, to the handling control unit via the instrument control unit.

* * * * *